United States Patent
Oda

(10) Patent No.: US 10,932,742 B2
(45) Date of Patent: Mar. 2, 2021

(54) IMAGE PROCESSING APPARATUS, RADIOGRAPHY SYSTEM, IMAGE PROCESSING METHOD, AND IMAGE PROCESSING PROGRAM

(71) Applicant: FUJIFILM Corporation, Tokyo (JP)

(72) Inventor: Yasufumi Oda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 70 days.

(21) Appl. No.: 16/432,667

(22) Filed: Jun. 5, 2019

(65) Prior Publication Data

US 2019/0374186 A1    Dec. 12, 2019

(30) Foreign Application Priority Data

Jun. 8, 2018 (JP) .............................. JP2018-110390

(51) Int. Cl.
G06K 9/00 (2006.01)
A61B 6/00 (2006.01)

(52) U.S. Cl.
CPC .............. *A61B 6/505* (2013.01); *A61B 6/482* (2013.01); *A61B 6/488* (2013.01); *A61B 6/50* (2013.01); *A61B 6/5217* (2013.01); *A61B 6/5282* (2013.01)

(58) Field of Classification Search
CPC ....... A61B 6/482; A61B 6/505; A61B 6/4233; A61B 6/4266; H04N 5/32
USPC ........... 382/132, 170; 378/108, 97; 250/584, 250/909
See application file for complete search history.

(56) References Cited

U.S. PATENT DOCUMENTS

| | | | |
|---|---|---|---|
| 4,903,310 A * | 2/1990 | Takeo | G06K 9/20 250/584 |
| 6,501,819 B2 | 12/2002 | Unger et al. | |
| 9,168,013 B2 | 10/2015 | Roessl et al. | |
| 10,634,799 B2 * | 4/2020 | Tajima | H04N 5/2251 |
| 2018/0028141 A1 | 2/2018 | Kuwabara | |

FOREIGN PATENT DOCUMENTS

JP    2018-23769 A    2/2018

OTHER PUBLICATIONS

Extended European Search Report, dated Oct. 31, 2019, for corresponding European Application No. 19176905.8.

* cited by examiner

*Primary Examiner* — Charlotte M Baker
(74) *Attorney, Agent, or Firm* — Birch, Stewart, Kolasch & Birch, LLP

(57) ABSTRACT

A CPU functions as an acquisition unit and a derivation unit. The acquisition unit acquires a first radiographic image and a second radiographic image respectively generated by a first radiation detector and a second radiation detectors which are irradiated with radiation with first energy emitted from a radiation source in preliminary imaging before main imaging from a radiography apparatus in which the first and second radiation detectors are arranged in a direction in which the radiation is emitted. The derivation unit derives the composition of a soft part of a subject, using the first and second radiographic images acquired by the acquisition unit, and derives second energy of the radiation emitted from the radiation source in the main imaging according to the derived composition of the soft part.

16 Claims, 11 Drawing Sheets

IMAGE PROCESSING APPARATUS, RADIOGRAPHY SYSTEM, IMAGE PROCESSING METHOD, AND IMAGE PROCESSING PROGRAM

CROSS-REFERENCE TO RELATED APPLICATION

This application claims priority from Japanese Patent Application No. 2018-110390, filed Jun. 8, 2018, the disclosure of which is incorporated by reference herein in its entirety.

BACKGROUND

Field of the Invention

The present disclosure relates to an image processing apparatus, a radiography system, an image processing method, and an image processing program.

Related Art

In recent years, a technique has been disclosed which performs preliminary imaging before main imaging and determines imaging conditions in the main imaging on the basis of the result of the preliminary imaging in a case in which a radiographic image of a subject is captured by a radiography apparatus (for example, see JP2018-023769A).

However, even in a case in which the imaging conditions are the same, the quality of a radiographic image captured by a radiography apparatus may vary depending on the subject. For example, since the quality of radiation transmitted through the subject varies depending on the body composition of the subject, such as the composition of a soft tissue of the subject, the quality of the radiographic image captured by radiation transmitted through the subject may vary.

However, in the technique disclosed in JP2018-023769A, the composition of the subject is not considered. Therefore, in some cases, a radiographic image with desired quality is not obtained in the main imaging.

In a case in which a radiographic image with desired quality is not obtained and a certain numerical value is derived from a radiographic image by, for example, a dual-energy X-ray absorptiometry (DXA) method for deriving the bone density of a subject from a radiographic image, the accuracy of the derived numerical value is likely to be reduced.

The present disclosure has been made in view of the above-mentioned problems and an object of the present disclosure is to provide an image processing apparatus, a radiography system, an image processing method, and an image processing program that can obtain a radiographic image with desired quality in main imaging.

SUMMARY

In order to achieve the object, according to a first aspect of the present disclosure, there is provided an image processing apparatus comprising: an acquisition unit that acquires a first radiographic image and a second radiographic image respectively generated by a first radiation detector and a second radiation detector which are irradiated with radiation with first energy emitted from a radiation source in preliminary imaging before main imaging from a radiography apparatus including the first and second radiation detectors in which a plurality of pixels, each of which includes a conversion element that generates a larger amount of charge as it is irradiated with a larger amount of radiation which has been emitted from the radiation source and then transmitted through a subject, are arranged and which are arranged in a direction in which the radiation is emitted; and a derivation unit that derives a composition of a soft tissue of the subject, using the first and second radiographic images acquired by the acquisition unit, and derives second energy of the radiation emitted from the radiation source in the main imaging according to the derived composition of the soft tissue.

According to a second aspect of the present disclosure, in the image processing apparatus according to the first aspect, as a percentage of muscle becomes higher than a percentage of fat in the composition of the soft tissue, the second energy may become lower.

According to a third aspect of the present disclosure, in the image processing apparatus according to the first or second aspect, the derivation unit may derive the composition of the soft tissue on the basis of a pixel value of a region corresponding to the soft tissue of the subject in the first radiographic image and a pixel value of a region corresponding to the soft tissue of the subject in the second radiographic image.

According to a fourth aspect of the present disclosure, in the image processing apparatus according to any one of the first to third aspects, the acquisition unit may further acquire a third radiographic image and a fourth radiographic image which are respectively generated by the first and second radiation detectors of the radiography apparatus irradiated with the radiation with the second energy emitted from the radiation source in the main imaging.

According to a fifth aspect of the present disclosure, in the image processing apparatus according to the fourth aspect, a number of pixels in each of the first radiographic image and the second radiographic image may be less than a number of pixels in each of the third radiographic image and the fourth radiographic image.

According to a sixth aspect of the present disclosure, in the image processing apparatus according to the fifth aspect, a size of each of the first radiographic image and the second radiographic image may correspond to a size of a region that is predetermined in order to derive the composition of the soft tissue.

According to a seventh aspect of the present disclosure, in the image processing apparatus according to any one of the fourth to sixth aspects, each of the first radiographic image and the second radiographic image may have a lower resolution than each of the third radiographic image and the fourth radiographic image.

According to an eighth aspect of the present disclosure, in the image processing apparatus according to the seventh aspect, each of the first radiographic image and the second radiographic image may be a radiographic image generated by reading charge in units of a plurality of predetermined pixels, and each of the third radiographic image and the fourth radiographic image may be a radiographic image generated by reading charge in units of one pixel.

According to a ninth aspect of the present disclosure, the image processing apparatus according to any one of the fourth to eighth aspects may further comprise a correction unit that corrects scattered ray components caused by scattered rays of the radiation included in each of the third radiographic image and the fourth radiographic image, using scattered ray correction data corresponding to the composition of the soft tissue.

According to a tenth aspect of the present disclosure, in the image processing apparatus according to any one of the fourth to ninth aspects, the derivation unit may further derive at least one of bone density or bone mineral content, using the third radiographic image and the fourth radiographic image acquired by the acquisition unit.

According to an eleventh aspect of the present disclosure, in the image processing apparatus according to any one of the first to tenth aspects, the first energy may be higher than the second energy.

According to a twelfth aspect of the present disclosure, in the image processing apparatus according to any one of the first to tenth aspects, the first energy may be lower than the second energy.

According to a thirteenth aspect of the present disclosure, in the image processing apparatus according to any one of the first to twelfth aspects, the preliminary imaging and the main imaging may be performed for the subject in a standing state.

According to a fourteenth aspect of the present disclosure, in the image processing apparatus according to any one of the first to thirteenth aspects, each of the first and second radiation detectors may comprise a light emitting layer that is irradiated with the radiation and emits light. The plurality of pixels of each of the first and second radiation detectors may receive the light, generate charge, and accumulate the charge. The light emitting layer of one of the first and second radiation detectors which is provided on an incident side of the radiation may include CsI and the light emitting layer of the other radiation detector may include GOS.

According to a fifteenth aspect of the present disclosure, there is provided a radiography system comprising: the image processing apparatus according to any one of the first to fourteenth aspects; and a radiography apparatus that outputs a first radiographic image and a second radiographic image to the image processing apparatus.

According to a sixteenth aspect of the present disclosure, there is provided an image processing method comprising: acquiring a first radiographic image and a second radiographic image respectively generated by a first radiation detector and a second radiation detector which are irradiated with radiation with first energy emitted from a radiation source in preliminary imaging before main imaging from a radiography apparatus including the first and second radiation detectors in which a plurality of pixels, each of which includes a conversion element that generates a larger amount of charge as it is irradiated with a larger amount of radiation which has been emitted from the radiation source and then transmitted through a subject, are arranged and which are arranged in a direction in which the radiation is emitted; deriving a composition of a soft tissue of the subject, using the acquired first and second radiographic images; and deriving second energy of the radiation emitted from the radiation source in the main imaging according to the derived composition of the soft tissue.

According to a seventeenth aspect of the present disclosure, there is provided an image processing program that causes a computer to perform: acquiring a first radiographic image and a second radiographic image respectively generated by a first radiation detector and a second radiation detector which are irradiated with radiation with first energy emitted from a radiation source in preliminary imaging before main imaging from a radiography apparatus including the first and second radiation detectors in which a plurality of pixels, each of which includes a conversion element that generates a larger amount of charge as it is irradiated with a larger amount of radiation which has been emitted from the radiation source and then transmitted through a subject, are arranged and which are arranged in a direction in which the radiation is emitted; deriving a composition of a soft tissue of the subject, using the acquired first and second radiographic images; and deriving second energy of the radiation emitted from the radiation source in the main imaging according to the derived composition of the soft tissue.

In order to achieve the object, an image processing apparatus according to the present disclosure includes a processor. The processor acquires a first radiographic image and a second radiographic image respectively generated by a first radiation detector and a second radiation detector which are irradiated with radiation with first energy emitted from a radiation source in preliminary imaging before main imaging from a radiography apparatus including the first and second radiation detectors in which a plurality of pixels, each of which includes a conversion element that generates a larger amount of charge as it is irradiated with a larger amount of radiation which has been emitted from the radiation source and then transmitted through a subject, are arranged and which are arranged in a direction in which the radiation is emitted, derives a composition of a soft tissue of the subject, using the acquired first and second radiographic images, and derives second energy of the radiation emitted from the radiation source in the main imaging according to the derived composition of the soft tissue.

According to the present disclosure, it is possible to obtain a radiographic image with desired quality in main imaging.

DETAILED DESCRIPTION

Hereinafter, embodiments of the present disclosure will be described in detail with reference to the drawings.

First Embodiment

Figure 1:
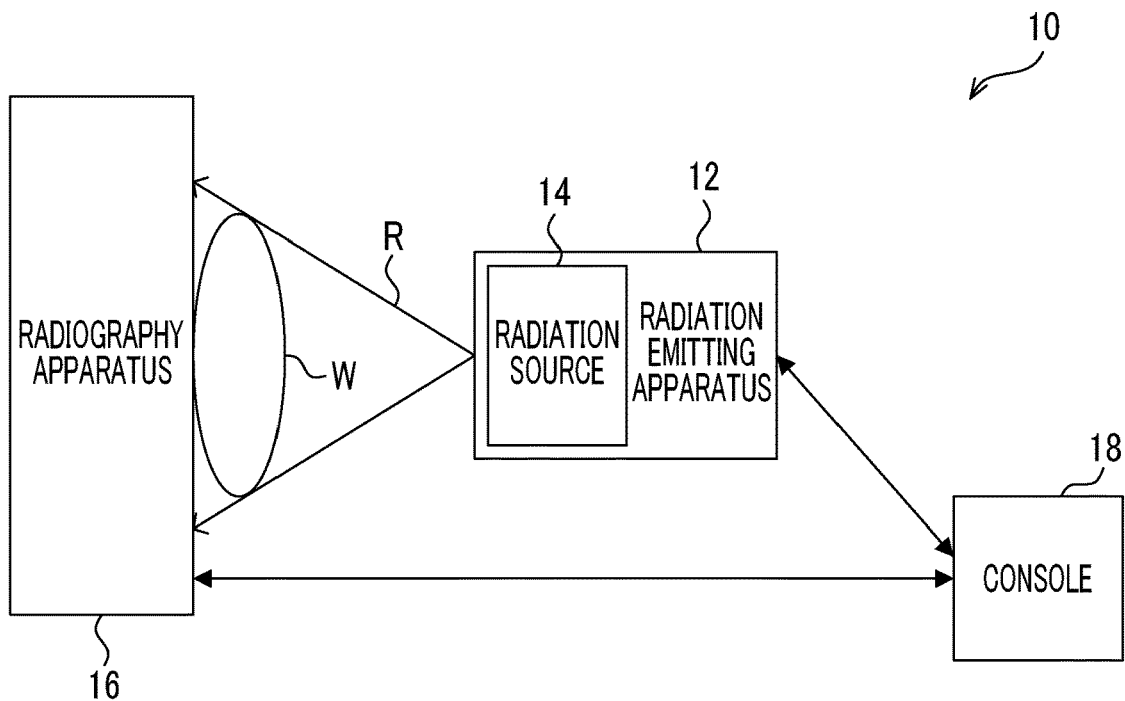
FIG. 1 is a block diagram illustrating an example of the configuration of a radiography system according to each embodiment.

First, the configuration of a radiography system 10 according to this embodiment will be described with reference to FIG. 1. As illustrated in FIG. 1, the radiography system 10 includes a radiation emitting apparatus 12, a radiography apparatus 16, and a console 18. The console 18 is an example of an image processing apparatus according to the present disclosure. In addition, for example, the radiography system 10 according to this embodiment captures a radiographic image of a subject W in a standing state.

The radiation emitting apparatus 12 according to this embodiment includes a radiation source 14 that irradiates a subject W, which is an example of an imaging target, with radiation R such as X-rays. The radiation emitting apparatus 12 according to this embodiment emits the radiation R with a cone-beam shape. An example of the radiation emitting apparatus 12 is a treatment cart. A method for commanding the radiation emitting apparatus 12 to emit the radiation R is not particularly limited. For example, in a case in which the radiation emitting apparatus 12 includes an irradiation button, a user, such as a radiology technician, may press the irradiation button to command the emission of the radiation R such that the radiation R is emitted from the radiation emitting apparatus 12. In addition, for example, the user, such as a radiology technician, may operate the console 18 to command the emission of the radiation R such that the radiation R is emitted from the radiation emitting apparatus 12.

In a case in which the command to emit the radiation R is received, the radiation emitting apparatus 12 emits the radiation R from the radiation source 14 according to set emission conditions, such as a tube voltage, a tube current, and an emission period. Hereinafter, the dose of the radiation R is simply referred to as "the amount of radiation".

Figure 2:
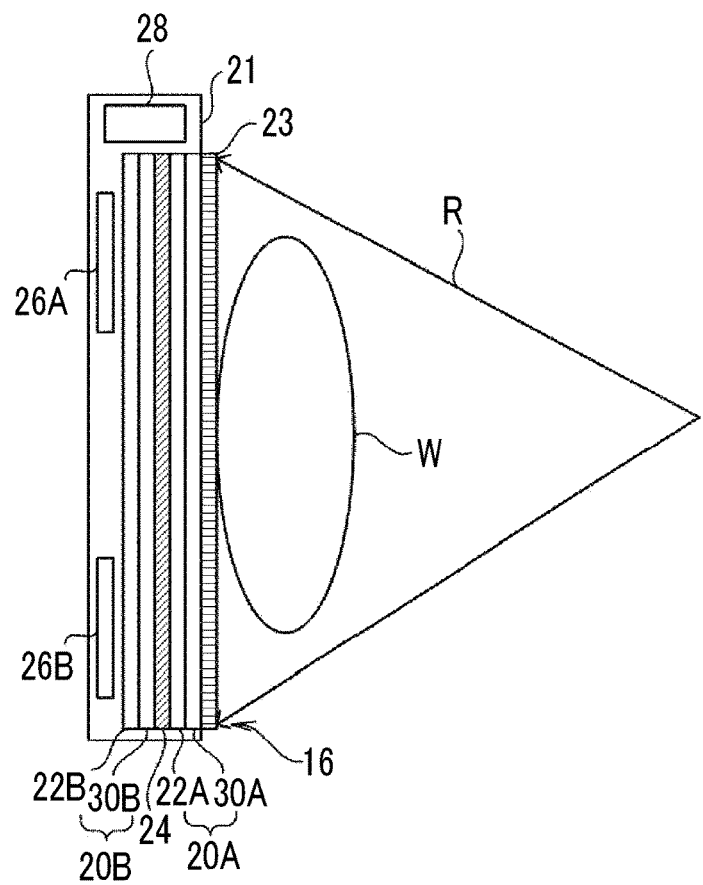
FIG. 2 is a side cross-sectional view illustrating an example of the configuration of a radiography apparatus according to a first embodiment.

Next, the configuration of the radiography apparatus 16 according to this embodiment will be described with reference to FIG. 2. As illustrated in FIG. 2, the radiography apparatus 16 includes a plate-shaped housing 21 that transmits the radiation R and has a waterproof, antibacterial, and airtight structure. The housing 21 includes a first radiation detector 20A and a second radiation detector 20B that detect the radiation R transmitted through the subject W. In addition, the housing 21 includes a radiation limitation member 24, a control substrate 26A, a control substrate 26B, and a case 28. The radiography apparatus 16 captures radiographic images of the subject W using the first radiation detector 20A and the second radiation detector 20B. Hereinafter, in a case in which the first radiation detector 20A and the second radiation detector 20B do not need to be distinguished from each other, they are generically referred to as "radiation detectors 20". In addition, a grid 23 for removing scattered rays is provided between the housing 21 and the subject W.

The first radiation detector 20A is provided on the incident side of the radiation R and the second radiation detector 20B is provided so as to be stacked on the side of the first radiation detector 20A from which the radiation R is transmitted and emitted. The first radiation detector 20A includes a thin film transistor (TFT) substrate 30A and a scintillator 22A which is an example of a light emitting layer that is irradiated with the radiation R and emits light. The TFT substrate 30A and the scintillator 22A are stacked in the order of the TFT substrate 30A and the scintillator 22A from the incident side of the radiation R. The term "stacked" means a state in which the first radiation detector 20A and the second radiation detector 20B overlap each other in a case in which the first radiation detector 20A and the second radiation detector 20B are seen from the incident side or the emission side of the radiation R in the radiography apparatus 16 and it does not matter how they overlap each other. A contact state between the first radiation detector 20A and the second radiation detector 20B and a state between the first radiation detector 20A and the second radiation detector 20B (in the stacking direction) are not particularly limited. For example, the first radiation detector 20A and the second radiation detector 20B, or the first radiation detector 20A, the radiation limitation member 24, and the second radiation detector 20B may overlap while coming into contact with each other or may overlap with a gap therebetween in the stacking direction. In addition, for example, other objects may be interposed between at least portions of a region interposed between the first radiation detector 20A and the second radiation detector 20B or other objects may be interposed between the portions with a gap therebetween. In this case, examples of other objects include a metal sheet, such as the radiation limitation member 24, a foam sheet for preventing damage, such as cracking, occurring in the radiation detector 20, and combinations thereof. However, other objects are not particularly limited. Objects corresponding to the required functions may be used.

The second radiation detector 20B includes a TFT substrate 30B and a scintillator 22B which is an example of the light emitting layer. The TFT substrate 30B and the scintillator 22B are stacked in the order of the TFT substrate 30B and the scintillator 22B from the incident side of the radiation R.

That is, the first radiation detector 20A and the second radiation detector 20B are irradiation side sampling (ISS) radiation detectors that are irradiated with the radiation R from the side of the TFT substrates 30A and 30B.

In the radiography apparatus 16 according to this embodiment, the scintillator 22A of the first radiation detector 20A and the scintillator 22B of the second radiation detector 20B have different compositions. Specifically, for example, the scintillator 22A includes CsI (TI) (cesium iodide having thallium added thereto) and the scintillator 22B includes gadolinium oxysulfide (GOS). In addition, a combination of the composition of the scintillator 22A and the composition of the scintillator 22B is not limited to the above-mentioned example and may be a combination of other compositions or a combination of the same compositions.

For example, the scintillators 22A and 22B have emission characteristics that vary depending on a thickness. As the thickness increases, the amount of light emitted increases and sensitivity increases. However, image quality deteriorates due to, for example, light scattering.

For example, in a case in which the scintillators 22A and 22B are formed by being filled with particles which are irradiated with the radiation R and emit light, such as GOS particles, as the diameter of the particle increases, the amount of light emitted increases and sensitivity increases. However, the amount of light scattering increases and the increase in the amount of light scattering affects adjacent pixels 32 (see FIG. 3), which results in the deterioration of image quality.

In addition, the scintillators 22A and 22B may have a multi-layered structure of a small-particle layer and a large-particle layer. For example, in a case in which each of the first radiation detector 20A and the second radiation detector 20B is irradiated with the radiation R from the scintillators 22A and 22B to the TFT substrates 30A and 30B unlike the radiography apparatus 16 according to this embodiment, the following occurs. That is, in this case, image blurring is small in the scintillators 22A and 22B in which a region close to the irradiation side of the radiation R is filled with small particles and a region close to the side of the TFT substrates 30A and 30B that is the emission side of the radiation R is filled with large particles. However, oblique components of light that is radially emitted by the small particles are less likely to reach the TFT substrates 30A and 30B and sensitivity is reduced. In addition, in a case in which the ratio of the region filled with small particles to the region filled with large particles is changed such that the number of layers formed by the region filled with large particles is larger than the number of layers formed by the region filled with small particles, sensitivity increases. However, in this case, light scattering affects adjacent pixels 32, which results in the deterioration of image quality.

As the filling rate of the particles increases, the sensitivity of the scintillators 22A and 22B increases. However, the amount of light scattering increases and image quality deteriorates. Here, the filling rate is a value obtained by dividing the total volume of the particles of the scintillator 22A or 22B by the volume of the scintillator 22A or 22B and multiplying the divided value by 100 (the total volume of the particles of the scintillator 22A or 22B/the volume of the scintillator 22A or 22B×100). In addition, powder is treated in the scintillators 22A and 22B. Therefore, in a case in which the filling rate is greater than 80 vol %, it is difficult to manufacture the scintillators 22A and 22B. For this reason, it is preferable that the filling rate is in the range of 50 vol % to 80 vol %.

In addition, the emission characteristics of the scintillators 22A and 22B vary depending on the doping amount of activator. As the doping amount of activator increases, the amount of light emitted tends to increase. However, the amount of light scattering increases and image quality deteriorates.

The emission characteristics of the scintillators 22A and 22B with respect to the radiation R vary depending on the material used for the scintillators 22A and 22B. For example, in a case in which each of the first radiation detector 20A and the second radiation detector 20B is irradiated with the radiation R from the scintillators 22A and 22B to the TFT substrates 30A and 30B unlike the radiography apparatus 16 according to this embodiment, the scintillator 22A is made of CsI (TI) and the scintillator 22B is made of GOS. In this case, in the scintillator 22A, emphasis is put on image quality and the absorptivity of the low-energy radiation R is relatively high. In the scintillator 22B, the absorptivity of the high-energy radiation R is relatively high.

In addition, the scintillator 22A has a columnar separated layer structure, which makes it possible to further improve image quality.

In a case in which reflecting layers (not illustrated) that transmit the radiation R and reflect visible light are formed on the surfaces of the scintillators 22A and 22B which are opposite to the TFT substrates 30A and 30B, light generated by the scintillators 22A and 22B is more effectively guided to the TFT substrates 30A and 30B and sensitivity is improved. A method for forming the reflecting layer is not particularly limited. For example, any one of a sputtering method, a vapor deposition method, or a coating method may be used. It is preferable that the reflecting layer is made of a material with high reflectance in an emission wavelength range of the scintillators 22A and 22B used. For example, the reflecting layer is made of Au, Ag, Cu, Al, Ni, and Ti. For example, in a case in which the scintillators 22A and 22B are made of GOS:Tb, the reflecting layer is preferably made of Ag, Al, and Cu that have high reflectance in a wavelength of 400 nm to 600 nm. In a case in which the thickness of the reflecting layer is less than 0.01 µm, reflectance is not obtained. Even in a case in which the thickness is greater than 3 µm, the effect of further improving the reflectance is not obtained. For this reason, it is preferable that the thickness of the reflecting layer is in the range of 0.01 µm to 3 µm.

Therefore, the characteristics of the scintillators 22A and 22B may vary depending on the diameter of particles, the multi-layered structure of particles, the filling rate of particles, the doping amount of activator, a material, a change in layer structure, and the shape of the reflecting layer.

In addition, the grid 23 that removes scattered rays generated by the transmission of the radiation R through the subject W from the radiation R transmitted through the subject W is provided on the side of the first radiation detector 20A on which the radiation R is incident side. For example, the effect of suppressing a reduction in the contrast of a radiographic image is obtained by the removal of the scattered rays from the radiation R and the quality of the radiographic image is improved.

The radiation limitation member 24 that limits the transmission of the radiation R is provided between the first radiation detector 20A and the second radiation detector 20B. An example of the radiation limitation member 24 is a plate-shaped member made of, for example, copper or tin. It is preferable that the thickness of the plate-shaped member is uniform in the range in which an error of a variation in the thickness is equal to or less than 1%. In a case in which the first radiation detector 20A sufficiently absorbs the radiation R, the radiation limitation member 24 may not be provided.

The control substrate 26A is provided so as to correspond to the first radiation detector 20A and electronic circuits, such as an image memory 56A and a control unit 58A which will be described below, are formed on the control substrate 26A. The control substrate 26B is provided so as to correspond to the second radiation detector 20B and electronic circuits, such as an image memory 56B and a control unit 58B which will be described below, are formed on the control substrate 26B. The control substrate 26A and the control substrate 26B are provided on the side of the second radiation detector 20B which is opposite to the incident side of the radiation R.

The case 28 is provided at a position (that is, outside the range of an imaging region) that does not overlap the radiation detector 20 at one end of the housing 21. For example, a power supply unit 70 which will be described below is accommodated in the case 28. The installation position of the case 28 is not particularly limited. For example, the case 28 may be provided at a position that overlaps the radiation detector 20 on the side of the second radiation detector 20B which is opposite to the incident side of the radiation.

Next, the configuration of a main portion of an electric system of the radiography apparatus 16 according to this embodiment will be described with reference to FIG. 3.

Figure 3:
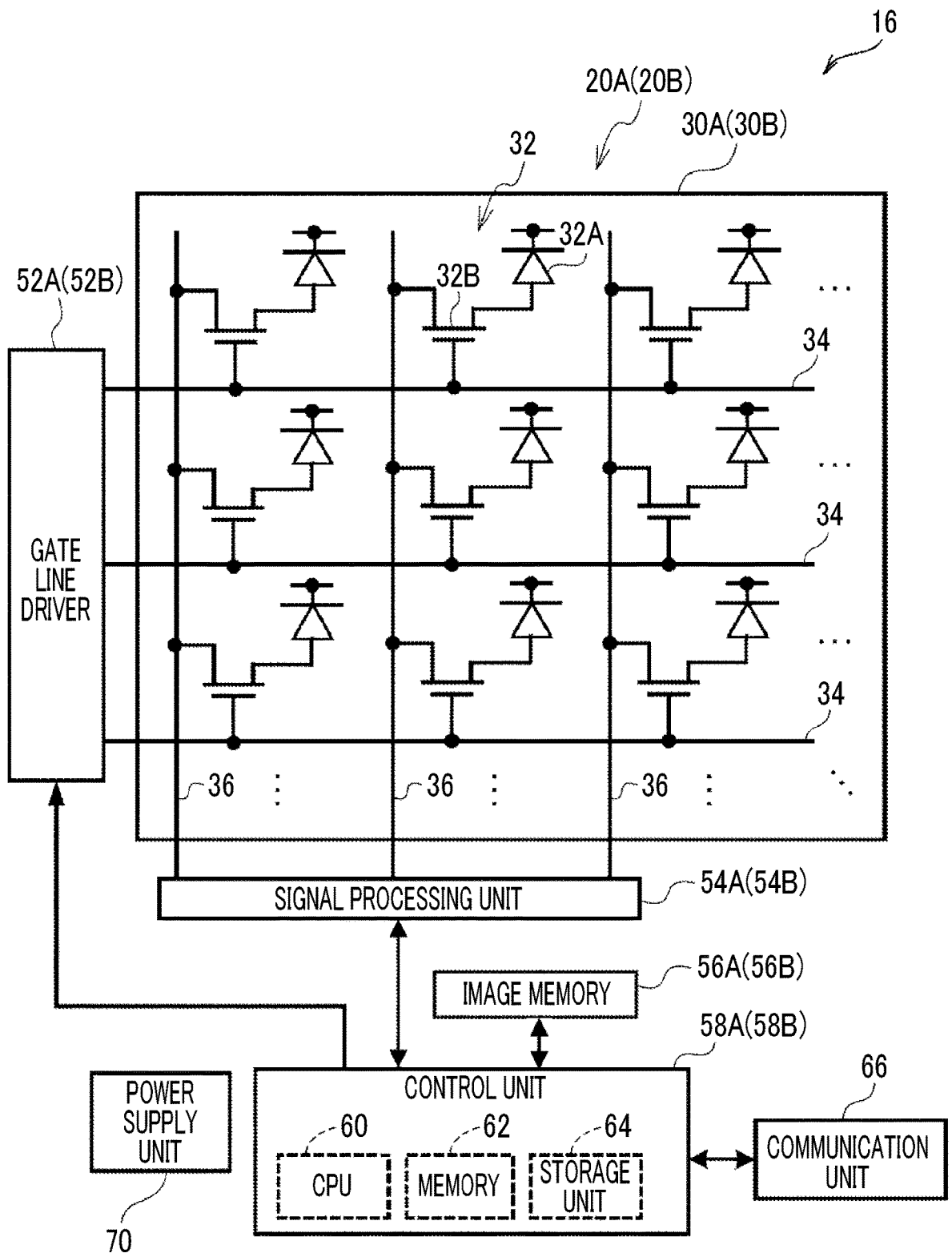
FIG. 3 is a block diagram illustrating an example of the configuration of a main portion of an electric system of a radiography apparatus according to each embodiment.

As illustrated in FIG. 3, a plurality of pixels 32 are two-dimensionally provided in one direction (a row direction in FIG. 3) and a cross direction (a column direction in FIG. 3) that intersects the one direction on the TFT substrate 30A. The pixel 32 includes a sensor unit 32A and a field effect thin film transistor (TFT; hereinafter, simply referred to as a "thin film transistor") 32B.

The sensor unit 32A includes, for example, an upper electrode, a lower electrode, and a photoelectric conversion film which are not illustrated, absorbs the light emitted from the scintillator 22A, generates charge, and accumulates the generated charge. The thin film transistor 32B converts the charge accumulated in the sensor unit 32A into an electric signal and outputs the electric signal. The sensor unit 32A is an example of a conversion element that generates a larger amount of charge as the amount of radiation becomes larger.

A plurality of gate lines 34 which extend in the one direction and are used to turn each thin film transistor 32B on and off are provided on the TFT substrate 30A. In addition, a plurality of data lines 36 which extend in the cross direction and are used to read out the charge through the thin film transistors 32B in an on state are provided on the TFT substrate 30A.

A gate line driver 52A is provided on one side of two adjacent sides of the TFT substrate 30A and a signal processing unit 54A is provided on the other side. Each gate line 34 of the TFT substrate 30A is connected to the gate line driver 52A and each data line 36 of the TFT substrate 30A is connected to the signal processing unit 54A.

The rows of the thin film transistors 32B of the TFT substrate 30A are sequentially turned on by the electric signals which are supplied from the gate line driver 52A through the gate lines 34. Then, the charge which has been read out by the thin film transistor 32B in an on state is transmitted as an electric signal through the data line 36 and is input to the signal processing unit 54A. In this way, charge is sequentially read out from each row of the thin film transistors and image data indicating a two-dimensional radiographic image is acquired.

The signal processing unit 54A includes amplifying circuits (not illustrated) for amplifying an input electric signal and sample-and-hold circuits (not illustrated) which are provided for each data line 36. The electric signal transmitted through each data line 36 is amplified by the amplifying circuit and is then held by the sample-and-hold circuit. A multiplexer and an analog/digital (A/D) converter are connected to the output side of the sample-and-hold circuit in this order. The electric signals held by each sample-and-hold circuit are sequentially (serially) input to the multiplexer and are sequentially selected by the multiplexer. Then, the selected electric signal is converted into digital image data by the A/D converter.

The control unit 58A which will be described below is connected to the signal processing unit 54A. The image data output from the A/D converter of the signal processing unit 54A is sequentially output to the control unit 58A. The image memory 56A is connected to the control unit 58A. The image data sequentially output from the signal processing unit 54A is sequentially stored in the image memory 56A under the control of the control unit 58A. The image memory 56A has memory capacity that can store a predetermined amount of image data. Whenever a radiographic image is captured, captured image data is sequentially stored in the image memory 56A.

The control unit 58A includes a central processing unit (CPU) 60, a memory 62 including, for example, a read only memory (ROM) and a random access memory (RAM), and a non-volatile storage unit 64 such as a flash memory. An example of the control unit 58A is a microcomputer.

A communication unit 66 is connected to the control unit 58A and transmits and receives various kinds of information to and from external apparatuses, such as the radiation emitting apparatus 12 and the console 18, using at least one of wireless communication or wired communication. The power supply unit 70 supplies power to each of the above-mentioned various circuits or elements (for example, the gate line driver 52A, the signal processing unit 54A, the image memory 56A, the control unit 58A, and the communication unit 66). In FIG. 3, lines for connecting the power supply unit 70 to various circuits or elements are not illustrated in order to avoid complication.

Components of the TFT substrate 30B, the gate line driver 52B, the signal processing unit 54B, the image memory 56B, and the control unit 58B of the second radiation detector 20B have the same configurations as the corresponding components of the first radiation detector 20A and thus the description thereof will not be repeated here. In addition, the control unit 58A and the control unit 58B are connected such that they can communicate with each other.

With the above-mentioned configuration, the radiography apparatus 16 according to this embodiment captures radiographic images using the first radiation detector 20A and the second radiation detector 20B. Hereinafter, the radiographic image captured by the first radiation detector 20A is referred to as a "first radiographic image" and image data indicating the first radiographic image is referred to as "first radiographic image data". In addition, hereinafter, the radiographic image captured by the second radiation detector 20B is referred to as a "second radiographic image" and image data indicating the second radiographic image is referred to as "second radiographic image data". In addition, in a case in which the "first radiographic image" and the "second radiographic image" are generically referred to, they are simply referred to as "radiographic images" similarly to the above.

Figure 4:
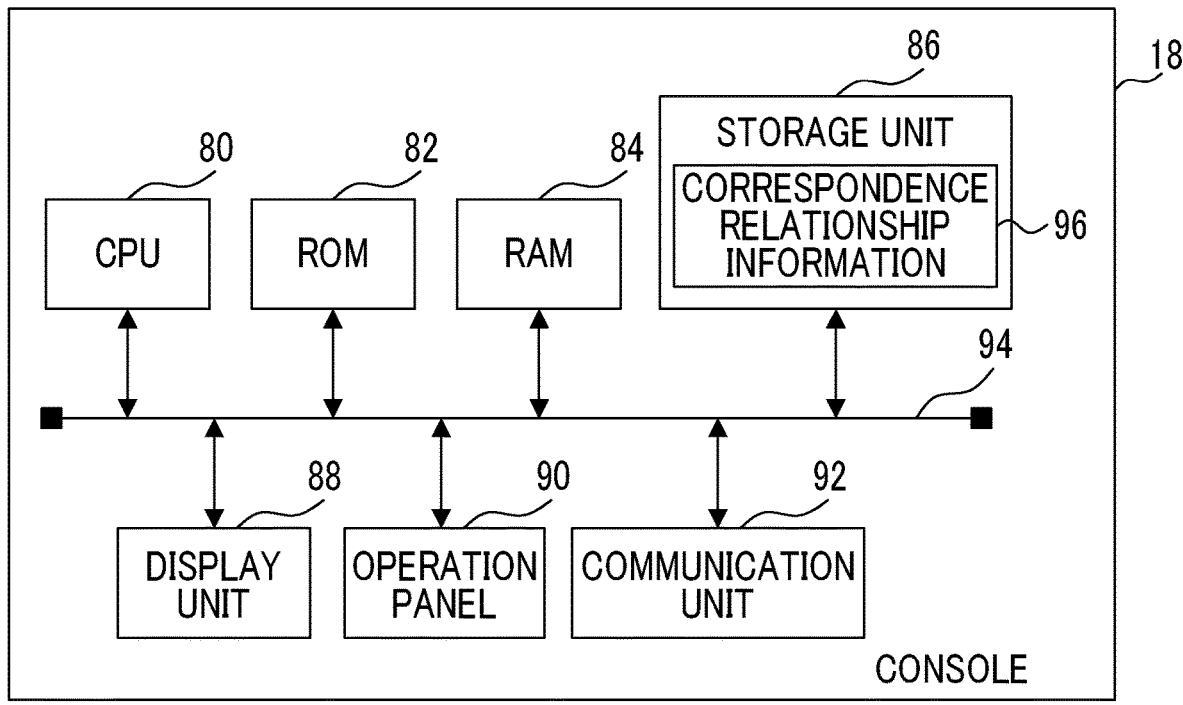
FIG. 4 is a block diagram illustrating an example of the configuration of a main portion of an electric system of a console according to the first embodiment.

Next, the configuration of the console 18 according to this embodiment will be described with reference to FIG. 4. As illustrated in FIG. 4, the console 18 comprises a CPU 80 that controls the overall operation of the console 18 and a ROM 82 in which, for example, various programs or various parameters are stored in advance. In addition, the console 18 comprises a RAM 84 that is used as, for example, a work area in a case in which the CPU 80 executes various programs and a non-volatile storage unit 86 such as a hard disk drive (HDD).

The console 18 further comprises a display unit 88 that displays, for example, an operation menu and a captured radiographic image and an operation panel 90 which includes a plurality of keys and to which various kinds of information or operation commands are input. In addition, the console 18 comprises a communication unit 92 that transmits and receives various kinds of information to and from external apparatuses, such as the radiation emitting apparatus 12 and the radiography apparatus 16, or external systems, such as a picture archiving and communication system (PACS) and a radiology information system (RIS), using at least one of wireless communication or wired communication. The CPU 80, the ROM 82, the RAM 84, the storage unit 86, the display unit 88, the operation panel 90, and the communication unit 92 are connected to each other through a bus 94.

The storage unit 86 stores correspondence relationship information 96 indicating a correspondence relationship between the composition of a soft tissue of the subject W and the energy of the radiation R emitted from the radiation source 14 in the main imaging, which will be described in detail below.

In the radiography apparatus 16 according to this embodiment, since the first radiation detector 20A and the radiation limitation member 24 absorb the radiation R, the amount of radiation that reaches the second radiation detector 20B is less than the amount of radiation that reaches the first radiation detector 20A. In addition, the radiation limitation member 24 generally has the characteristic that it absorbs a larger number of soft-ray components than hard-ray components in energy forming the radiation R, which depends on the material forming the radiation limitation member 24. Therefore, the energy distribution of the radiation R that reaches the second radiation detector 20B has a larger number of hard-ray components than the energy distribution of the radiation R that reaches the first radiation detector 20A.

In this embodiment, for example, about 50% of the radiation R that has reached the first radiation detector 20A is absorbed by the first radiation detector 20A and is used to capture a radiographic image. In addition, about 60% of the radiation R that has passed through the first radiation detector 20A and reached the radiation limitation member 24 is absorbed by the radiation limitation member 24. About 50% of the radiation R that has passed through the first radiation detector 20A and the radiation limitation member 24 and reached the second radiation detector 20B is absorbed by the second radiation detector 20B and is used to capture a radiographic image. Since the absorptivity of radiation by the radiation detector 20 and the radiation limitation member 24 varies depending on the energy of the radiation R, the shape of a spectrum changes.

That is, the amount of radiation used by the second radiation detector 20B to capture a radiographic image is about 20% of the amount of radiation used by the first radiation detector 20A to capture a radiographic image. In addition, the ratio of the amount of radiation used by the second radiation detector 20B to capture a radiographic image to the amount of radiation used by the first radiation detector 20A to capture a radiographic image is not limited to the above-mentioned ratio. However, it is preferable that the amount of radiation used by the second radiation detector 20B to capture a radiographic image is equal to or greater than 10% of the amount of radiation used by the first radiation detector 20A to capture a radiographic image in terms of diagnosis.

Figure 5:
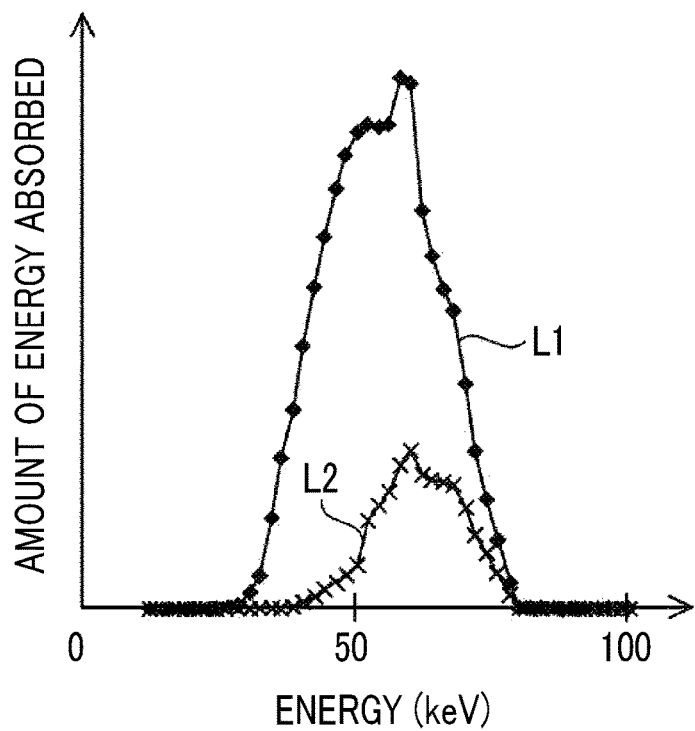
FIG. 5 is a graph illustrating the amount of radiation that reaches each of a first radiation detector and a second radiation detector.

Low-energy components of the radiation R are absorbed first. The radiation R absorbed by each of the first radiation detector 20A and the second radiation detector 20B will be described with reference to FIG. 5. In FIG. 5, the vertical axis indicates the amount of radiation R absorbed and the horizontal axis indicates the energy of the radiation R in a case in which the tube voltage of the radiation source 14 is 80 kV. In addition, in FIG. 5, a solid line L1 indicates the relationship between the energy of the radiation R absorbed by the first radiation detector 20A and the amount of radiation R absorbed. In addition, in FIG. 5, a solid line L2 indicates the relationship between the energy of the radiation R absorbed by the second radiation detector 20B and the amount of radiation R absorbed. Since the low-energy components of the radiation R are absorbed first, for example, as illustrated in FIG. 5, the energy components of the radiation R that reaches the second radiation detector 20B do not include the low-energy components of the energy components of the radiation R that reaches the first radiation detector 20A. That is, the energy of the radiation R emitted to the first radiation detector 20A is different from the energy of the radiation R emitted to the second radiation detector 20B through the first radiation detector 20A. Therefore, in the radiography apparatus 16 according to this embodiment, the radiation detectors 20 are irradiated with the radiations R having different energy levels (radiation R with a first energy level and radiation R with a second energy level) and radiographic images are generated by the radiation detectors 20.

The console 18 according to this embodiment acquires radiographic image data generated by the radiation detectors 20 irradiated with the radiations R having different energy levels. In addition, the console 18 derives the ratio of the values of the corresponding pixels of first radiographic image data and second radiographic image data and generates image data for deriving the bone density of the subject W. Hereinafter, the image data for deriving the bone density of the subject W is referred to as "DXA image data" and an image indicated by the DXA image data is referred to as a "DXA image". Specifically, the console 18 performs log conversion for each pixel value of each of the first radiographic image data and the second radiographic image data. Then, the console 18 generates DXA image data, using an energy subtraction process that subtracts image data obtained by performing log conversion for the second radiographic image data from image data obtained by performing log conversion for the first radiographic image data for each corresponding pixel.

Figure 6:
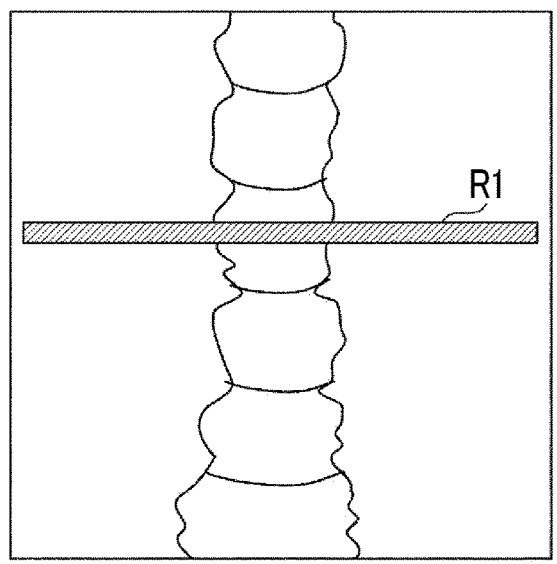
FIG. 6 is a front view illustrating an example of a region from which a DXA profile used to derive bone density is to be derived.

In addition, for example, as illustrated in FIG. 6, the console 18 according to this embodiment derives bone density from each pixel value (that is, the ratio of the values of the corresponding pixels of the first radiographic image and the second radiographic image and a difference value between the pixel values in a log image) of a bone part of the subject W in the cross-sectional direction (the horizontal direction in the example illustrated in FIG. 6) in the DXA image.

Figure 7:
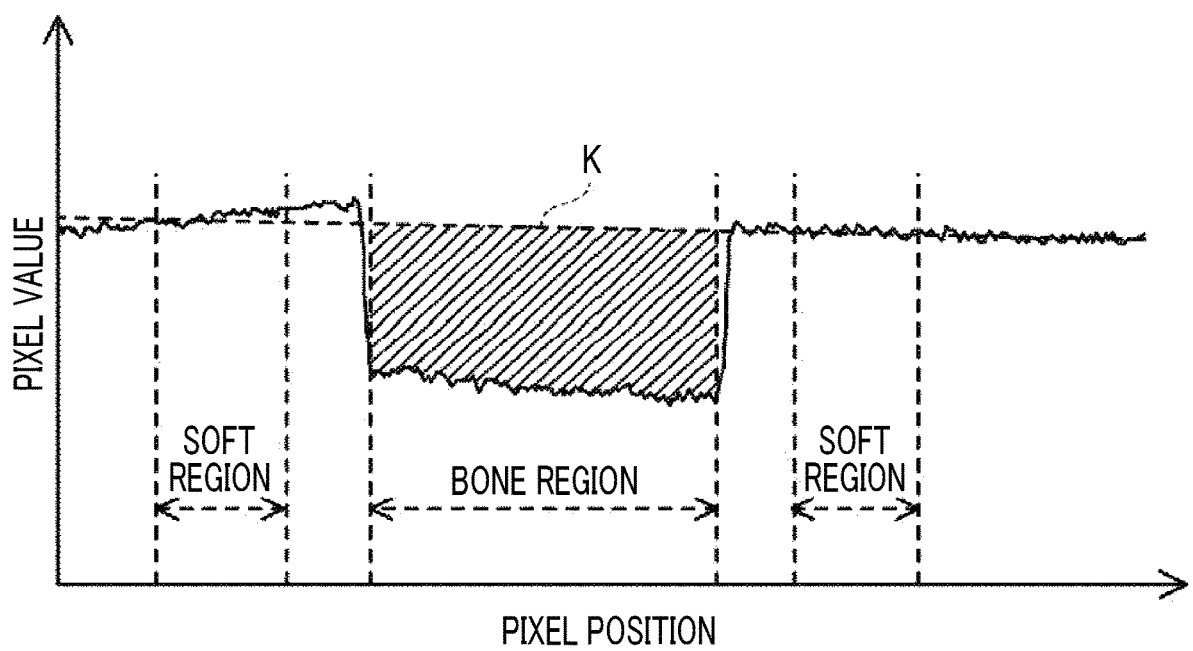
FIG. 7 is a graph illustrating a bone density derivation process.

FIG. 7 illustrates the value of each pixel in a region RI of the DXA image illustrated in FIG. 6. In FIG. 7, the horizontal axis indicates a pixel position in the horizontal direction of FIG. 6. In addition, in FIG. 7, the vertical axis indicates an average value of the values of a plurality of pixels in the vertical direction of FIG. 6 at each pixel position in the horizontal direction of FIG. 6. Hereinafter, a data group of the pixel values at each pixel position along the horizontal direction of FIG. 6 which is illustrated in FIG. 7 is referred to as a "DXA profile".

As illustrated in FIG. 7, for the pixel values in the DXA profile, a pixel value at a pixel position corresponding to the bone tissue of the subject W is less than a pixel value at a pixel position corresponding to the soft tissue. The console 18 according to this embodiment derives the average value of the pixel values in soft tissue regions (hereinafter, referred to as "soft regions") on both sides of a bone tissue region (hereinafter, referred to as a "bone region") and derives a straight line (hereinafter, referred to as a "reference line") K that connects the average values derived at the pixel positions in a central portion of each soft region. In addition, the console 18 adds the differences between the reference line K and the pixel values at each pixel position in the bone region to derive the area of the bone region (the area of a hatched portion illustrated in FIG. 7). The area is a value corresponding to the bone mass of the subject W.

In addition, the console 18 divides the derived area by the number of pixels corresponding to the width of the bone region to derive the difference between the pixel values of the bone region and the soft region per unit number of pixels. The difference is a value corresponding to the bone density of the subject W. Then, the console 18 multiplies the derived difference between the pixel values of the bone region and the soft region per unit number of pixels by a predetermined unit conversion coefficient to derive the bone density of the subject W. In this embodiment, the pixel position of the region RI used to derive the DXA profile in the DXA image data, the pixel position of the soft region of the DXA profile, and the pixel position of the bone region are predetermined according to, for example, the subject W and an imaging part.

Figure 8:
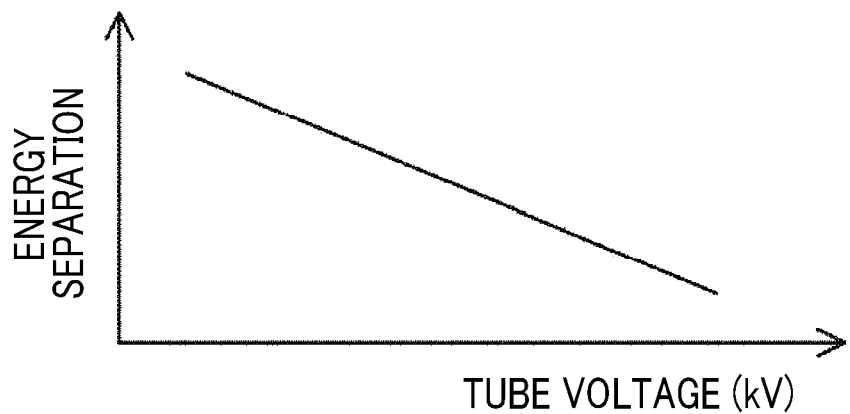
FIG. 8 is a graph illustrating a relationship between a tube voltage of radiation emitted from a radiation source and energy separation.

In a case in which bone density is derived by the DXA method as described above, it is preferable that the degree of energy separation of the radiation R in the first radiation detector 20A and the second radiation detector 20B is high in order to increase the accuracy of derivation. As illustrated in FIG. 8, the magnitude of energy separation and the tube voltage of the radiation source 14 for emitting the radiation R have the relationship in which the magnitude of energy separation becomes smaller as the tube voltage becomes higher. In other words, there is a reciprocal relationship between energy separation and the tube voltage. Therefore, it is preferable to reduce the tube voltage in order to increase the accuracy of deriving bone density. However, in a case in which the tube voltage is low, the radiation R with low energy has a characteristic that it is likely to be absorbed by the human body. Therefore, the exposure of the subject W to radiation increases. It is preferable to increase the tube voltage in terms of the exposure of the subject W to radiation. However, in this case, the degree of energy separation is reduced from the above-mentioned relationship. As a result, the accuracy of deriving bone density is reduced.

As such, increasing the accuracy of deriving bone density and reducing the exposure of the subject W to radiation are contrary to each other and have a so-called trade-off relationship therebetween. Whether to attach importance to the derivation of bone density or the exposure of the subject W to radiation is determined according to the policy. From these points of view, it is desirable that the radiation emitting apparatus 12 emits the radiation R with optimum energy to acquire a radiographic image.

Figure 9:
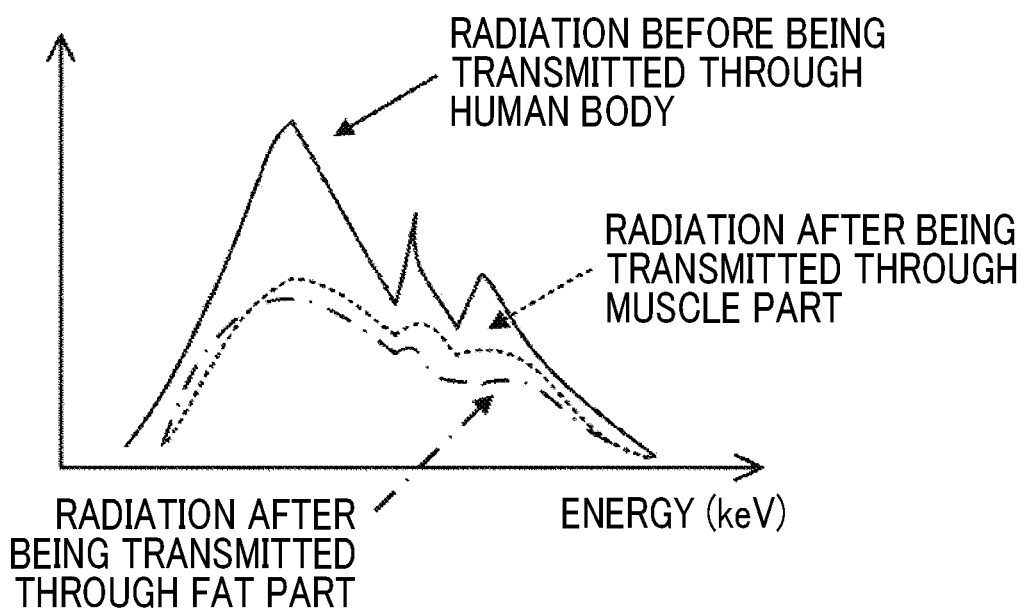
FIG. 9 is a graph illustrating a difference in energy spectrum between radiation before being transmitted through the human body (subject) and radiation after being transmitted through the human body.

Even in a case in which the energy of the radiation R emitted from the radiation source 14 is the same, the quality of the radiographic image captured by the radiography apparatus 16 may vary depending on the subject W. For example, as illustrated in FIG. 9, the intensity of the radiation R transmitted through the subject W that is the human body is lower than the intensity of the radiation R before the radiation R is incident on the subject W. In addition, among the radiations R transmitted through the subject W, the radiation R transmitted through a muscle part and the radiation R transmitted through a fat part have different energy spectrums. As can be seen from FIGS. 8 and 9, the energy spectrum of the radiation R that is transmitted through the subject W and then emitted to the radiography apparatus 16 depends on the body composition of the subject W, specifically, the ratio of muscle and fat. As the percentage of muscle becomes higher the percentage of fat, the degree of energy separation becomes lower.

Therefore, the radiography system 10 according to this embodiment performs control such that, as the percentage of muscle increases, the energy of the radiation R emitted from the radiation source 14 is reduced to optimize the energy of the radiation R which is transmitted through the subject W and is then emitted to the radiography apparatus 16, regardless of the body composition of the subject W. Specifically, in the radiography system 10 according to this embodiment, the radiation R with predetermined energy is emitted from the radiation source 14 to the subject W and the radiography apparatus 16 captures a radiographic image of the subject W. Then, the energy of the radiation R emitted from the radiation source 14 in order to capture a radiographic image for DXA is derived according to the composition of the soft tissue of the subject W derived from the obtained radiographic image. Hereinafter, in this embodiment, capturing a final radiographic image corresponding to the user's request, such as capturing a radiographic image for DXA, is referred to as "main imaging" and capturing a radiographic image for deriving the amount of radiation R emitted from the radiation source 14 in the preliminary imaging before the main imaging is referred to as "preliminary imaging". In addition, the energy of the radiation R emitted from the radiation source 14 in the preliminary imaging according to this embodiment corresponds to an example of "first energy" according to the present disclosure and the energy of the radiation R emitted from the radiation source 14 in the main imaging according to this embodiment corresponds to an example of "second energy" according to the present disclosure.

Figure 10:
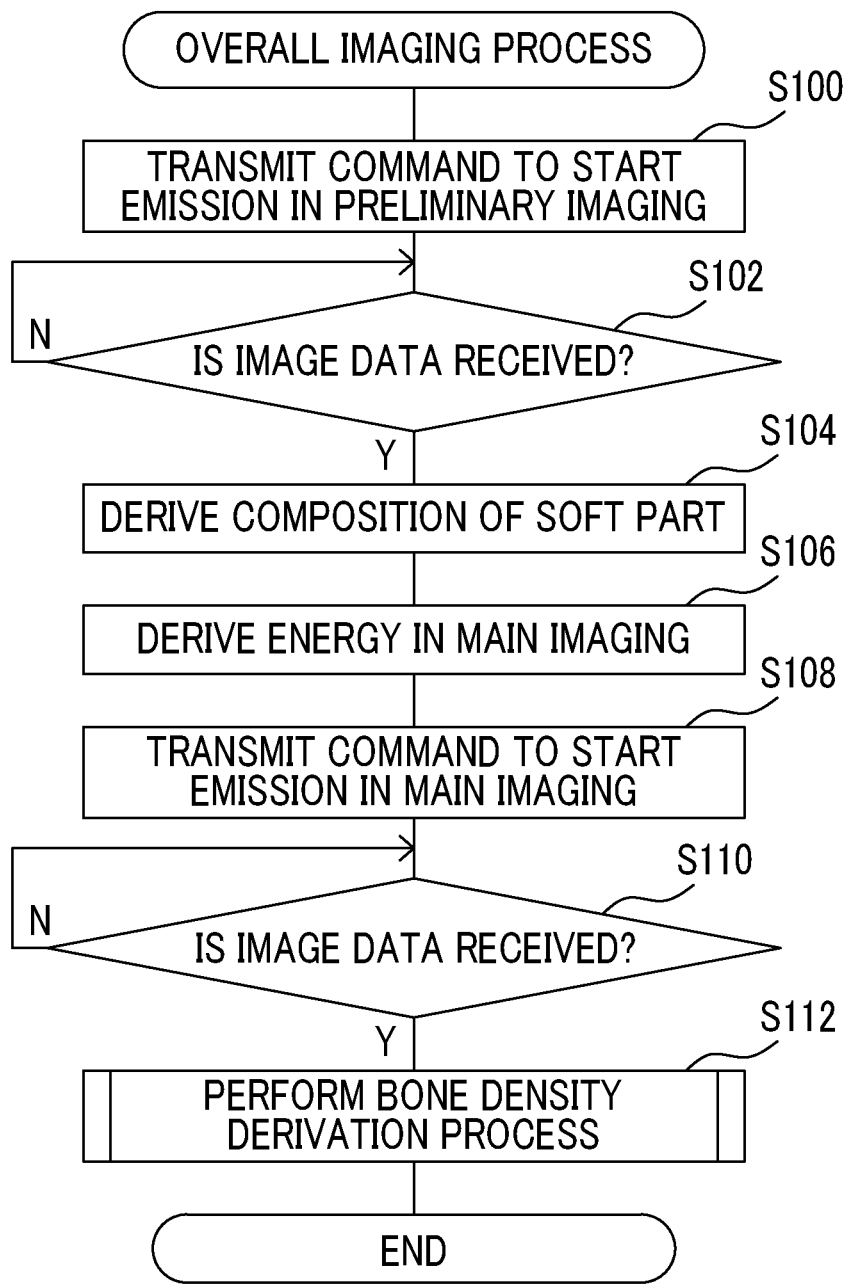
FIG. 10 is a flowchart illustrating an example of an overall imaging process according to the first embodiment.

Next, the operation of the radiography system 10 according to this embodiment will be described. FIG. 10 is a flowchart illustrating the process flow of an overall imaging processing program executed by the CPU 80 of the console 18 in a case in which the user inputs the name of the subject W, an imaging part, and an imaging menu through the operation panel 90. The overall imaging processing program is installed in the storage unit 86 of the console 18 in advance.

Figure 11:
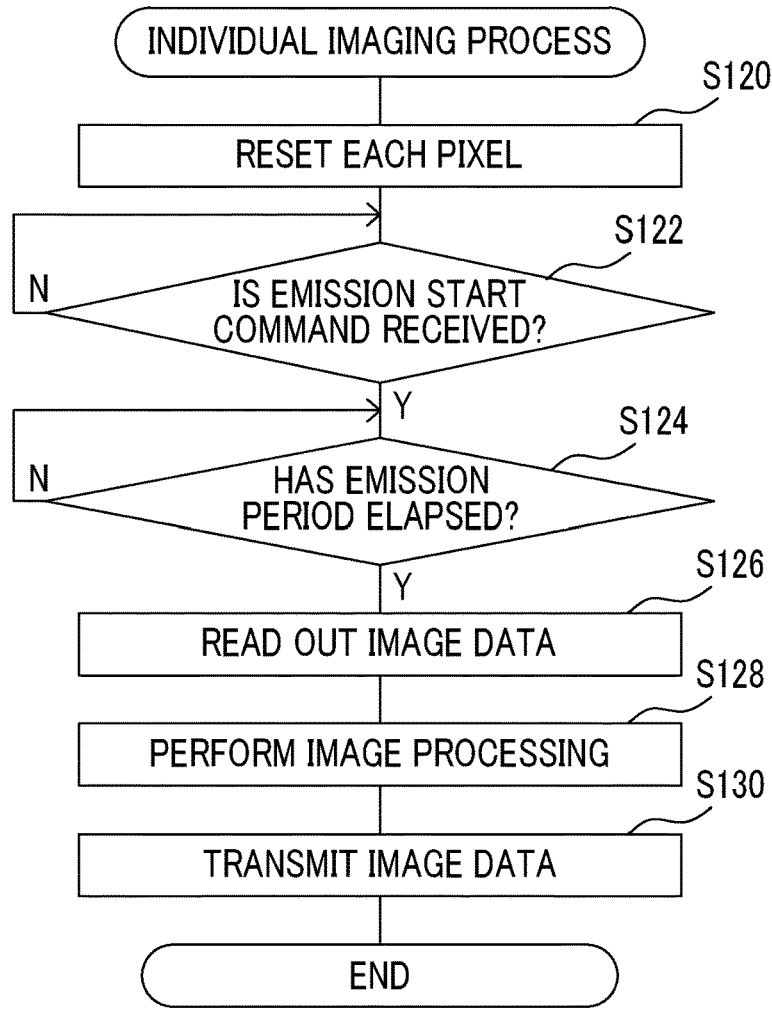
FIG. 11 is a flowchart illustrating an example of an individual imaging process according to the first embodiment.

FIG. 11 is a flowchart illustrating the process flow of an individual imaging processing program executed by the control unit 58A of the radiography apparatus 16, for example, in a case in which an imaging command is input to the radiography apparatus 16. The individual imaging processing program is installed in the ROM of the memory 62 of the control unit 58A in advance. In addition, the individual imaging processing program is installed in the ROM of the memory 62 of the control unit 58B in advance and is executed by the control unit 58B of the radiography apparatus 16 in a case in which the radiography apparatus 16 is turned on. In the individual imaging process illustrated in FIG. 11, the control unit 58A and the control unit 58B perform the same process. Therefore, hereinafter, only a case in which the individual imaging process is performed by the control unit 58A will be described and the description of a case in which the individual imaging process is performed by the control unit 58B will be omitted.

In Step S100 illustrated in FIG. 10, the CPU 80 transmits information for preliminary imaging included in the input imaging menu to the radiography apparatus 16 through the communication unit 92 and transmits the emission conditions of the radiation R to the radiation emitting apparatus 12 through the communication unit 92. In addition, the information for preliminary imaging is not limited to the aspect in which the information is included in the imaging menu. For example, the information for preliminary imaging may be predetermined in the console 18.

Then, the CPU 80 transmits a command to start the emission of the radiation R to the radiography apparatus 16 and the radiation emitting apparatus 12 through the communication unit 92. In a case in which the emission conditions and the emission start command transmitted from the console 18 are received, the radiation emitting apparatus 12 starts the emission of the radiation R according to the received emission conditions. The radiation emitting apparatus 12 may include an irradiation button. In this case, the radiation emitting apparatus 12 receives the emission conditions and the emission start command transmitted from the console 18 and starts the emission of the radiation R according to the received emission conditions in a case in which the irradiation button is pressed.

In the next Step S102, the CPU 80 waits until the first radiographic image data of the first radiographic image captured by the first radiation detector 20A and the second radiographic image data of the second radiographic image captured by the second radiation detector 20B are received. In a case in which the CPU 80 receives the first radiographic image data and the second radiographic image data through the communication unit 92, the determination result in Step S102 is "Yes" and the process proceeds to Step S104.

Figure 12:
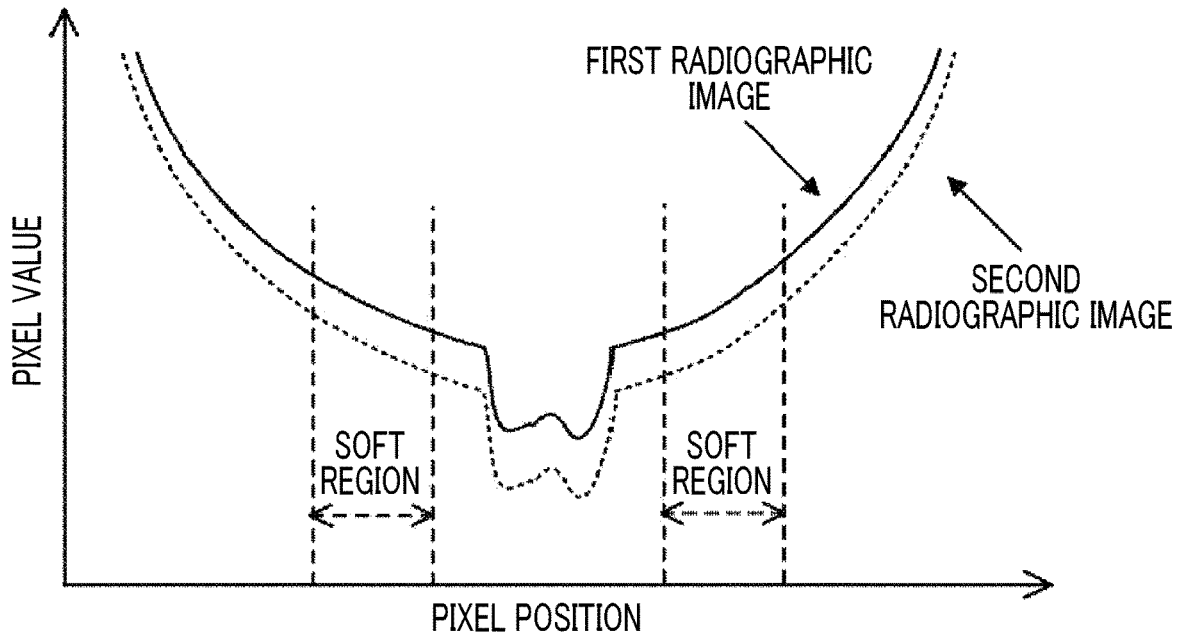
FIG. 12 is a graph illustrating a difference between the pixel values of a first radiographic image and a second radiographic image.

In Step S104, the CPU 80 derives the composition of a soft tissue of the subject W. In an example illustrated in FIG. 12, the energy of the radiation R emitted is different in the first radiographic image generated by the first radiation detector 20A and the second radiographic image generated by the second radiation detector 20B as described above. Therefore, even in a case in which the position (region) with respect to the subject W is the same, the value of the pixel of the radiographic image varies. For this reason, in this embodiment, as illustrated in FIG. 12, a soft region is derived from each of the first radiographic image and the second radiographic image and the composition of a soft tissue of the soft region which depends on the percentage of muscle (fat) is derived by the following Expression (1): the composition of the soft tissue=the pixel value of the soft region of the first radiographic image÷the pixel value of the soft region of the second radiographic image (1). Here, the soft region used to derive the composition of the soft tissue may be the same as or different from the soft region applied to derive the bone density.

Then, in Step S106, the CPU 80 derives the energy of the radiation R emitted from the radiation source 14 in the main imaging (hereinafter, referred to as "the energy of the radiation R in the main imaging") on the basis of the composition of the soft tissue derived in Step S104. For example, in this embodiment, the correspondence relationship information 96 indicating the correspondence relationship between the composition of the soft tissue and the energy of the radiation R in the main imaging is stored in the storage unit 86 in advance before the main imaging. Therefore, the CPU 80 derives the energy of the radiation R in the main imaging which corresponds to the composition of the soft tissue derived in Step S104, with reference to the correspondence relationship information 96 stored in the storage unit 86. In addition, a method for deriving the energy of the radiation R in the main imaging is not particularly limited. For example, instead of the correspondence relationship information 96, information indicating the correspondence relationship among the composition of the soft tissue, the energy of the radiation R in the preliminary imaging, and the energy of the radiation R in the main imaging may be used or a derivation expression for deriving the energy of the radiation R in the main imaging from the composition of the soft tissue and the energy of the radiation R in the preliminary imaging may be used. In addition, these correspondence relationships and the derivation expression may be obtained in advance by, for example, experiments using a phantom. In any derivation method, in this embodiment, as the percentage of muscle becomes higher than the percentage of fat, the energy of the radiation R in the main imaging becomes lower.

Then, in Step S108, the CPU 80 transmits the energy of the radiation R in the main imaging derived in Step S106 and information included in the input imaging menu to the radiography apparatus 16 through the communication unit 92 and transmits the emission conditions of the radiation R to the radiation emitting apparatus 12 through the communication unit 92.

Similarly to the preliminary imaging, the CPU 80 transmits a command to start the emission of the radiation R to the radiography apparatus 16 and the radiation emitting apparatus 12 through the communication unit 92. In a case in which the emission conditions and the command to start the emission of radiation transmitted from the console 18 are received, the radiation emitting apparatus 12 starts the emission of the radiation R with the energy derived in Step S106 according to the received emission conditions.

Then, in Step S510, the CPU 80 waits until the first radiographic image data of the first radiographic image captured by the first radiation detector 20A and the second radiographic image data of the second radiographic image captured by the second radiation detector 20B are received. In a case in which the CPU 80 receives the first radiographic image data and the second radiographic image data through the communication unit 92, the determination result in Step S110 is "Yes" and the process proceeds to Step S112. In addition, in the main imaging according to this embodiment, the first radiographic image captured by the first radiation detector 20A is an example of a third radiographic image according to the present disclosure and the second radiographic image captured by the second radiation detector 20B is an example of a fourth radiographic image according to the present disclosure.

Figure 13:
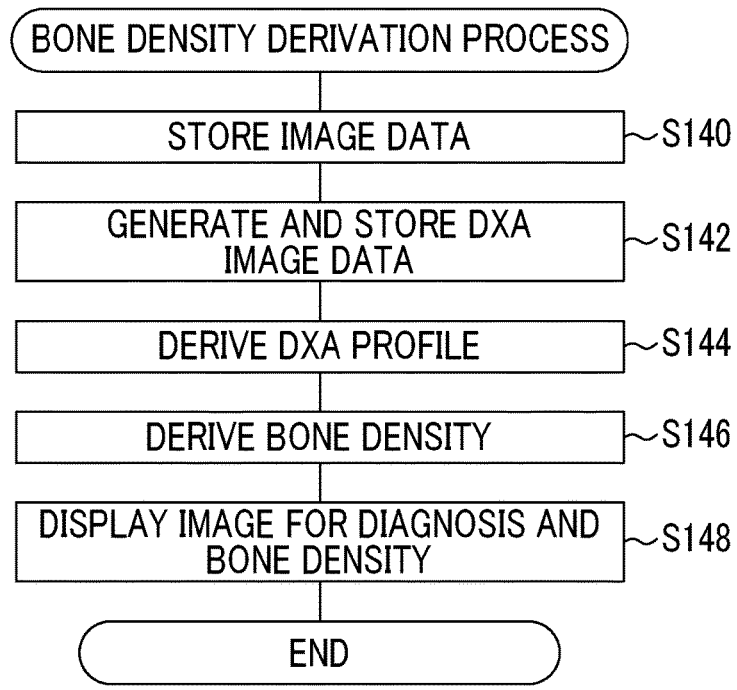
FIG. 13 is a flowchart illustrating an example of a bone density derivation process according to the first embodiment.

In Step S112, the CPU 80 performs a bone density derivation process whose example is illustrated in FIG. 13 and then ends the overall imaging process.

In the first radiation detector 20A and the second radiation detector 20B, the individual imaging process whose example is illustrated in FIG. 11 is performed as described above. In the radiography system 10 according to this embodiment, in a case in which the imaging menu includes information instructing the derivation of bone density, an individual imaging process for the preliminary imaging ends and then an individual imaging process for the main imaging is performed. In addition, since the individual imaging process for the preliminary imaging and the individual imaging process for the main imaging are the same process, they are not distinguished from each other in the following description.

In Step S120 of the individual imaging process illustrated in FIG. 11, the control unit 58A performs a reset operation which emits the charge accumulated in the sensor unit 32A of each pixel 32 in the first radiation detector 20A. In addition, the control unit 58A may perform the reset operation in Step S120 only once, may repeatedly perform the reset operation a predetermined number of times or at a predetermined time interval, or may repeatedly perform the reset operation until the determination result in Step S122, which will be described below, becomes "Yes".

In Step S122, the control unit 58A is in a standby state until a command to start the emission of the radiation R is received. In a case in which the control unit 58A receives the emission start command transmitted from the console 18 in Step S100 of the overall imaging process through the communication unit 66, the determination result in Step S122 is "Yes" and the process proceeds to Step S124. In a case in which the radiation emitting apparatus 12 comprises an irradiation button and the control unit 58A receives the emission start command transmitted from the console 18 and information indicating that the irradiation button has been pressed through the communication unit 66, the determination result in Step S122 is "Yes".

For example, in a case in which the irradiation button is pressed, the radiation emitting apparatus 12 may directly transmit information indicating that the irradiation button has been pressed to the radiography apparatus 16 or may transmit the information to the radiography apparatus 16 through the console 18.

In Step S124, the control unit 58A waits for an emission period that is included in the information transmitted from the console 18 in Step S100 of the overall imaging process. Specifically, the determination result in Step S124 is "No" until the emission period elapses. In a case in which the emission period comes, the determination result in Step S124 is "Yes" and the process proceeds to Step S126.

In Step S126, the control unit 58A controls the gate line driver 52A such that the gate line driver 52A sequentially outputs an on signal to each of the gate lines 34 of the first radiation detector 20A for a predetermined period. Then, the rows of the thin film transistors 32B connected to each gate line 34 are sequentially turned on and the charge accumulated in each sensor unit 32A in each row sequentially flows as an electric signal to each data line 36. Then, the electric signal which has flowed to each data line 36 is converted into digital image data by the signal processing unit 54A and is stored in the image memory 56A.

Then, in Step S128, the control unit 58A performs image processing for performing various types of correction, such as offset correction and gain correction, for the image data stored in the image memory 56A in Step S126. Then, in Step S130, the control unit 58A transmits the image data (first radiographic image data) subjected to the image processing in Step S128 to the console 18 through the communication unit 66 and then ends the individual imaging process.

In the preliminary imaging, in a case in which the console 18 receives the first radiographic image data and the second radiographic image data transmitted by the process in Step S130, the determination result in Step S102 of the overall imaging process (see FIG. 10) is "Yes" and the process proceeds to Step S104 to derive the composition of the soft tissue. In addition, in the main imaging, in a case in which the console 18 receives the first radiographic image data and the second radiographic image data transmitted by the process in Step S130, the determination result in Step S110 of the overall imaging process (see FIG. 10) is "Yes" and the process proceeds to Step S112 to perform the bone density derivation process illustrated in FIG. 13.

In Step S140 of the bone density derivation process illustrated in FIG. 13, the CPU 80 stores the first radiographic image data and the second radiographic image data received in Step S102 of the overall imaging process (see FIG. 10) in the storage unit 86.

Then, in Step S142, the CPU 80 generates DXA image data using the first radiographic image data and the second radiographic image data stored in the storage unit 86. Specifically, the CPU 80 performs log conversion for each pixel value of the first radiographic image data and the second radiographic image data. Then, the CPU 80 generates DXA image data, using an energy subtraction process that subtracts image data obtained by performing log conversion for the second radiographic image data from image data obtained by performing log conversion for the first radiographic image data for each corresponding pixel. Then, the CPU 80 stores the generated DXA image data in the storage unit 86.

A method for determining the corresponding pixels of the first radiographic image data and the second radiographic image data is not particularly limited. For example, the amount of positional deviation between first radiographic image data and second radiographic image data is calculated from a difference in the position of a marker between the first radiographic image data and the second radiographic image data captured by the radiography apparatus 16 in a state in which the marker is placed in advance. Then, the corresponding pixels of the first radiographic image data and the second radiographic image data are determined on the basis of the calculated amount of positional deviation.

In this case, for example, the amount of positional deviation between first radiographic image data and second radiographic image data may be calculated from a difference in the position of a marker between the first radiographic image data and the second radiographic image data obtained by capturing the image of the marker together with the subject W in a case in which the image of the subject W is captured. In addition, for example, the amount of positional deviation between first radiographic image data and second radiographic image data may be calculated on the basis of the structure of the subject in the first radiographic image data and the second radiographic image data obtained by capturing the image of the subject W.

Then, in Step S144, the CPU 80 derives a DXA profile using the DXA image data generated in Step S142. Then, in Step S146, the CPU 80 derives an integrated value of the differences between the reference line K and the pixel values of the bone region in the DXA profile derived in Step S144. In addition, the CPU 80 divides the derived integrated value by the number of pixels corresponding to the width of the bone region in the DXA profile. Then, the CPU 80 multiplies the value obtained by the division by a unit conversion coefficient to derive the bone density of the subject W.

Then, in Step S148, the CPU 80 displays the first radiographic image indicated by the first radiographic image data as an image for diagnosis on the display unit 88 and displays the bone density derived in Step S146 on the display unit 88. Then, the CPU 80 ends the bone density derivation process.

In addition, the CPU 80 may generate image data (hereinafter, referred to as "ES image data") indicating an energy subtraction image (hereinafter, referred to as an "ES image"), using the first radiographic image data and the second radiographic image data. In this case, for example, the CPU 80 subtracts image data obtained by multiplying the first radiographic image data by a predetermined coefficient from image data obtained by multiplying the second radiographic image data by a predetermined coefficient for each corresponding pixel. The CPU 80 generates ES image data indicating an ES image in which the soft tissues have been removed and the bone tissues have been highlighted, using the subtraction. In this example, in Step S148, the CPU 80 may display an ES image in which the bone tissues have been highlighted on the display unit 88, instead of the image for diagnosis.

In addition, the CPU 80 may specify the edge of a bone region from the ES image in which the bone tissues have been highlighted and may use the specification result as a pixel position corresponding to the bone region in the DXA image data. In this case, for example, the CPU 80 estimates the approximate range of the bone region on the basis of the imaging part included in the imaging menu. Then, the CPU 80 detects pixels that are disposed in the vicinity of the pixels, of which the differential values are equal to or greater than a predetermined value, as the pixels forming the edge (end) of the bone region in the estimated range to specify the bone region.

In this case, the CPU 80 may specify, as the soft region, a region which has a predetermined area including pixels that are separated from the specified edge of the bone region by a distance corresponding to a predetermined number of pixels in a predetermined direction in which the region becomes further away from the bone part. In this case, the CPU 80 may use the specification result as a pixel position corresponding to the soft tissue in the DXA image data.

As such, the console 18 according to this embodiment derives the composition of the soft tissue of the subject W from the radiographic image obtained by the preliminary imaging and derives the energy of the radiation R in the main imaging according to the derived composition of the soft tissue. The console 18 according to this embodiment directs the radiation source 14 to emit the radiation R with the derived energy for the main imaging. Therefore, it is possible to optimize the energy of the radiation R emitted to the radiography apparatus 16, regardless of the body composition of the subject W.

Second Embodiment

Hereinafter, a second embodiment of the technology according to the present disclosure will be described in detail. In addition, since the configuration of a radiography system 10 according to this embodiment is the same as that in the first embodiment except for information stored in the storage unit 86 of the console 18 (see FIGS. 1 to 4), the description thereof will not be repeated here. Further, components having the same functions as those in the first embodiment are denoted by the same reference numerals and the description thereof will not be repeated.

Figure 14:
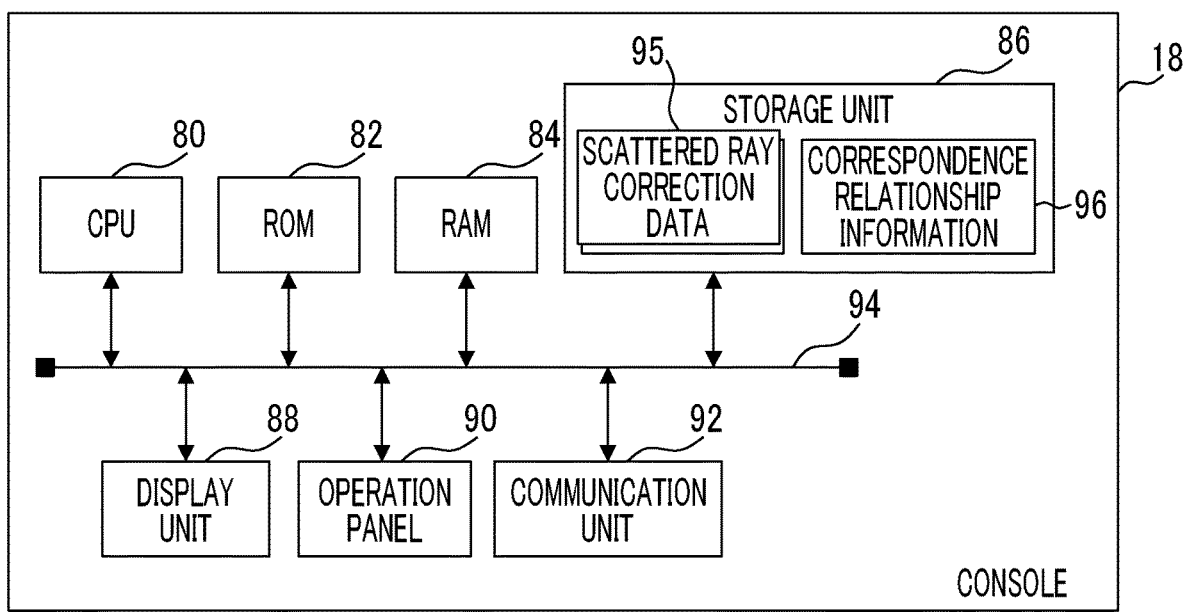
FIG. 14 is a block diagram illustrating an example of the configuration of a main portion of an electric system of a console according to a second embodiment.

As in an example illustrated in FIG. 14, the storage unit 86 of the console 18 according to this embodiment further stores scattered ray correction data 95 for correcting scattered ray components which will be described below.

As described above, a predetermined amount of scattered rays is removed by the grid 23. However, components (hereinafter, "scattered ray components") caused by the scattered rays which have not been removed by the grid 23 are included in the first radiographic image and the second radiographic image. In particular, in a DXA method for deriving the bone density of the subject W, the numerical value of the derived bone density is also affected by the amount of scattered rays which have not been removed by the grid 23. For this reason, the console 18 according to this embodiment corrects the scattered ray components included in the first radiographic image and the second radiographic image, using the scattered ray correction data 95. In addition, the intensity and spread of the scattered rays vary depending on various conditions. Therefore, in this embodiment, calibration is performed according to various conditions and the scattered ray correction data 95 obtained by the calibration is stored in the storage unit 86 so as to be associated with each combination of the conditions. Hereinafter, the calibration will be described in detail.

Figure 15A:
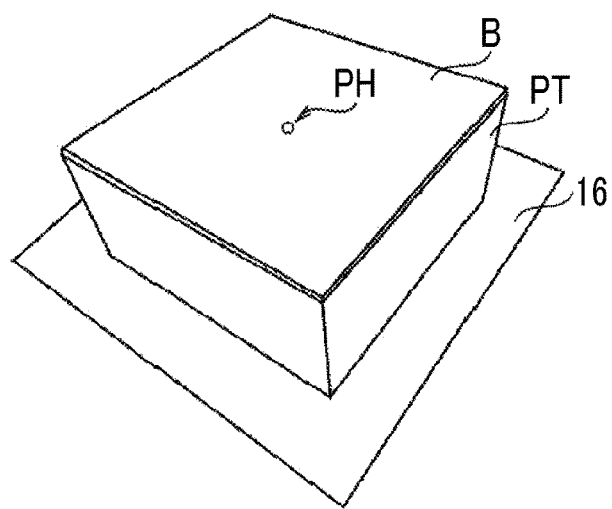
FIG. 15A is a perspective view illustrating calibration according to the second embodiment.

The scattered ray correction data 95 according to this embodiment will be described with reference to FIGS. 15A to 16B. In this embodiment, as illustrated in FIG. 15A, a plurality of scattered ray correction data items 95 which have been obtained in advance by calibration using a phantom PT simulating the human body and a flat-plate-shaped radiation shielding member B shielding the radiation R are stored in the storage unit 86. A pinhole PH is formed in a central portion of the radiation shielding member B. The phantom PT simulates the human body using a material corresponding to the soft tissues of the human body and a material corresponding to the bone tissues of the human body. For example, acryl or urethane can be applied as the material corresponding to the soft tissues of the human body. Further, in this embodiment, a plurality of types of phantoms PT having different ratios of muscle and fat which are the soft tissues of the human body are prepared. In addition, for example, hydroxyapatite can be applied as the material corresponding to the bone tissues of the human body. Hereinafter, the scattered ray correction data 95 will be described in detail.

Figure 15B:
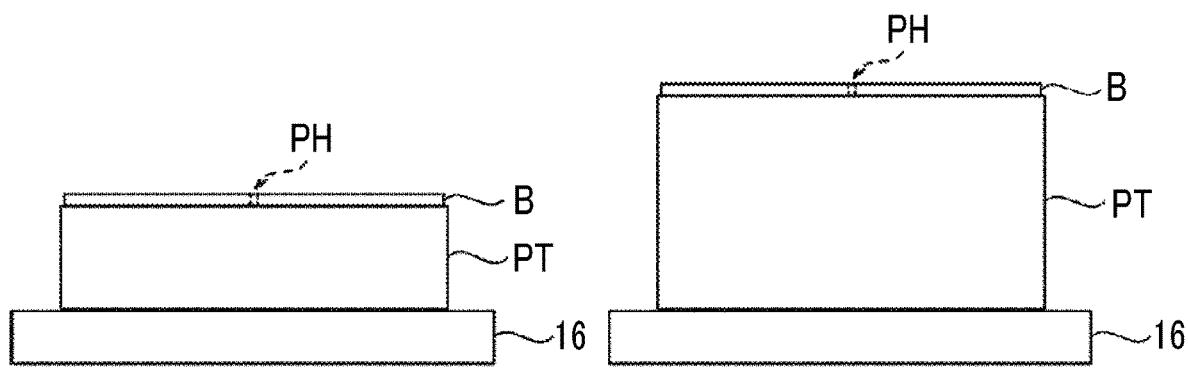
FIG. 15B is a side view illustrating calibration in a subject region according to the second embodiment.

In each radiation detector 20, different scattered rays are generated in a region (hereinafter, referred to as a "subject region") irradiated with the radiation R that has been transmitted through the subject W and a region (hereinafter, referred to as a "directly irradiated region") directly irradiated with the radiation R that has not been transmitted through the subject W. Therefore, in this embodiment, for calibration related to the subject region, as illustrated in FIG. 15B, the phantom PT is disposed on the side of the radiography apparatus 16 on which the radiation R is incident, the radiation shielding member B is disposed on the side of the phantom PT on which the radiation R is incident, and the radiation R is emitted from the radiation emitting apparatus 12 for a predetermined period. The console 18 generates the scattered ray correction data 95 with image data obtained from each radiation detector 20 in this case and stores the generated scattered ray correction data 95 in the storage unit 86.

Figure 16A:
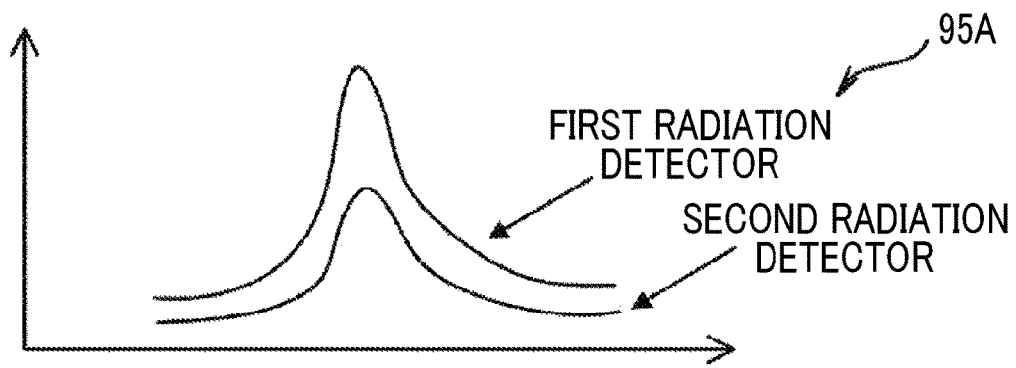
FIG. 16A is a graph illustrating an example of scattered ray correction data according to the second embodiment.
Figure 16B:
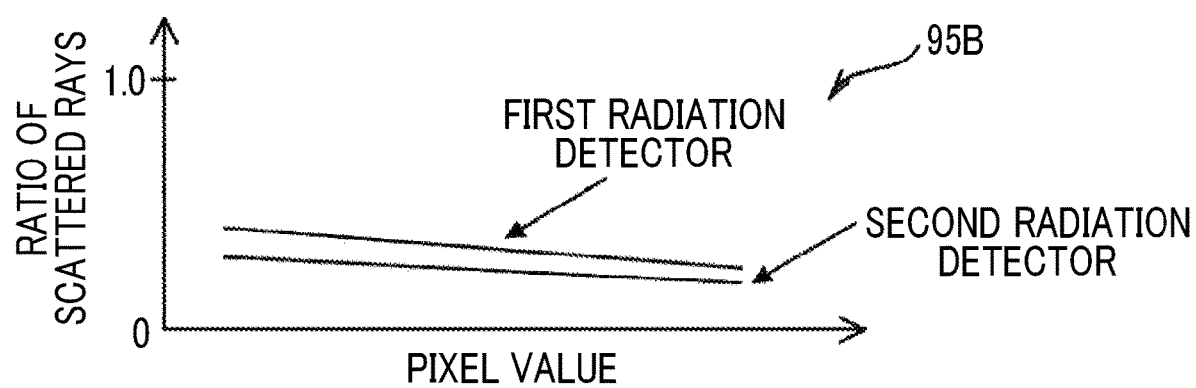
FIG. 16B is a graph illustrating an example of the scattered ray correction data according to the second embodiment.

For example, the scattered ray correction data 95 corresponding to the subject region includes information indicating the spread of scattered rays illustrated in FIG. 16A and information indicating the intensity of scattered rays illustrated in FIG. 16B. The information indicating the spread of scattered rays illustrated in FIG. 16A is also referred to as a point spread function (PSF). In addition, the information indicating the intensity of scattered rays illustrated in FIG. 16B is information in which a pixel value per unit amount of radiation is associated with the ratio of scattered rays at the pixel value. Hereinafter, in the scattered ray correction data 95, the information indicating the spread of scattered rays is referred to as a PSF 95A and the information indicating the intensity of scattered rays is referred to intensity information 95B.

As described above, the energy of the radiation R emitted to the first radiation detector 20A is different from the energy of the radiation R emitted to the second radiation detector 20B. Therefore, as illustrated in FIGS. 16A and 16B, the information indicating the spread of scattered rays and the information indicating the intensity of scattered rays are different in the first radiation detector 20A and the second radiation detector 20B. For this reason, in this embodiment, the scattered ray correction data 95 obtained from the first radiation detector 20A by calibration is stored in the storage unit 86 so as to be associated with the first radiation detector 20A. In addition, the scattered ray correction data 95 obtained from the second radiation detector 20B by calibration is stored in the storage unit 86 so as to be associated with the second radiation detector 20B.

In addition, different scattered rays are generated according to the body composition of the subject W. Therefore, in this embodiment, the scattered ray correction data 95 obtained by calibration using a plurality of types of phantoms PT having different body compositions (the ratios of muscle and fat) is also stored in the storage unit 86 so as to be associated with the composition of the soft tissue.

Figure 15C:
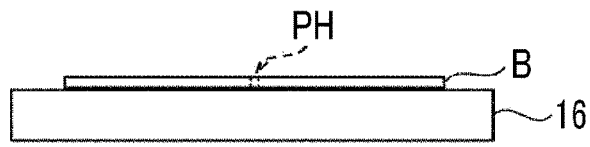
FIG. 15C is a side view illustrating calibration in a directly irradiated region according to the second embodiment.

In contrast, for calibration related to the directly irradiated region, as illustrated in FIG. 15C, the radiation shielding member B is disposed on the side of the radiography apparatus 16 on which the radiation R is incident and the radiation R is emitted from the radiation emitting apparatus 12 for a predetermined period. The console 18 derives information indicating the spread of scattered rays, using image data obtained from each radiation detector 20 in this case. In addition, the console 18 derives the amount of scattered rays from the amount of radiation and derives the amount of scattered rays per unit amount of radiation as information indicating the intensity of scattered rays. Then, the console 18 stores the derived information indicating the spread of scattered rays and the derived information indicating the intensity of scattered rays as the scattered ray correction data 95 corresponding to the directly irradiated region in the storage unit 86.

In addition, different scattered rays are generated according to imaging conditions. Therefore, in this embodiment, calibration is performed each of the imaging conditions used in the facility in which the radiography system 10 is provided and the scattered ray correction data 95 is stored in the storage unit 86 so as to be associated with the imaging conditions. The imaging conditions include, for example, a material (for example, tungsten) forming a bulb of the radiation source 14, a tube voltage, a material (for example, copper) forming the radiation limitation member 24, the characteristics of the grid 23 (for example, a grid ratio, grid density, and a convergence distance), and a source image distance (SID). The SID indicates a distance from the radiation source 14 to a surface for detecting the radiation R in the first radiation detector 20A. In addition, the imaging conditions include the quality of a material (for example, carbon) forming the surface of a case accommodating the radiography apparatus 16 on which the radiation R is incident. Examples of the surface of the case accommodating the radiography apparatus 16 on which the radiation R is incident include a top plate of a decubitus imaging table and a decorative cover of an upright imaging table.

The scattered ray correction data 95 according to this embodiment is stored in the storage unit 86 so as to be associated with a plurality of imaging conditions in which at least the tube voltages and the body compositions of the subject W are different from each other. In other words, the scattered ray correction data 95 is stored in the storage unit 86 so as to be associated with a plurality of different energy levels corresponding to the tube voltages.

Next, the operation of the radiography system 10 according to this embodiment will be described with reference to FIG. 17. Since an individual imaging process performed in the console 18 according to this embodiment is the same as the individual imaging process (see FIG. 11) according to the first embodiment, the description thereof will not be repeated. In this embodiment, since a bone density derivation process performed in an overall imaging process is different from the bone density derivation process (see FIGS. 10 and 13) performed in the overall imaging process according to the first embodiment, the bone density derivation process according to this embodiment will be described.

Figure 17:
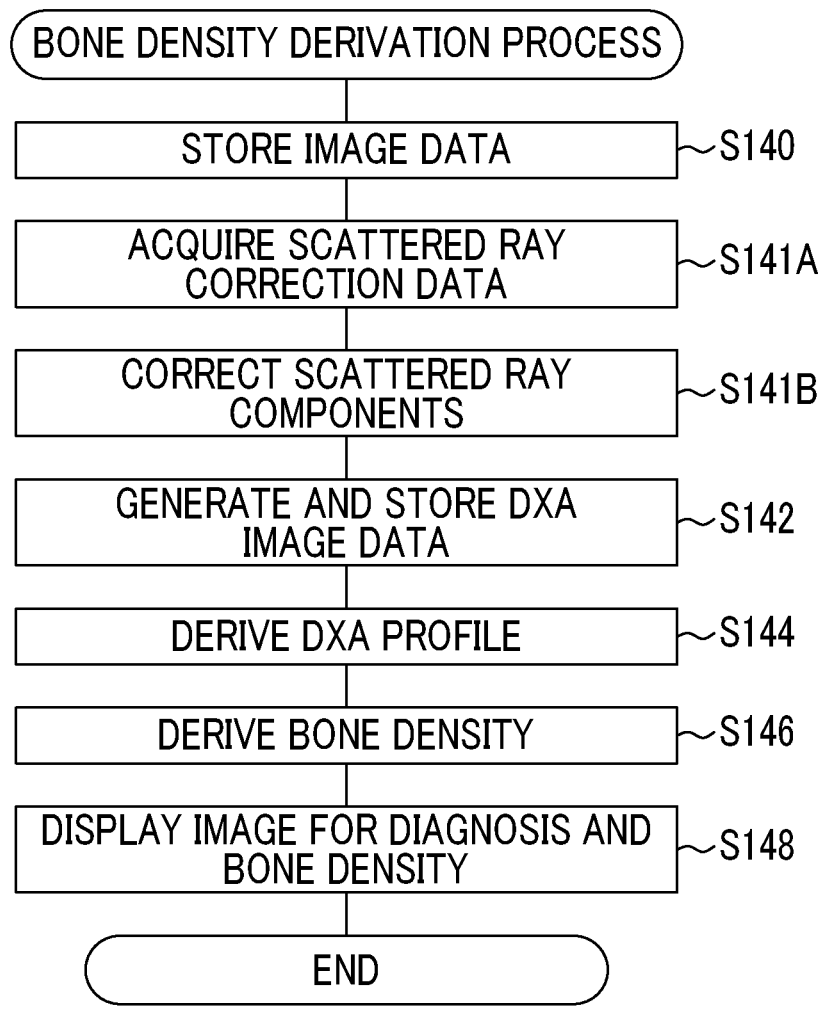
FIG. 17 is a flowchart illustrating an example of a bone density derivation process according to the second embodiment.

FIG. 17 is a flowchart illustrating an example of the bone density derivation process performed in the console 18 according to this embodiment. The bone density derivation process illustrated in FIG. 17 differs from the bone density derivation process according to the first embodiment in that processes in Step S141A and Step S141B are performed between Step S140 and Step S142.

In Step S140 of FIG. 17, the CPU 80 stores each of the first radiographic image data and the second radiographic image data received in Step S102 of the overall imaging process (see FIG. 10) in the storage unit 86.

Then, in Step S141A, the CPU 80 acquires the scattered ray correction data 95 associated with the composition of the soft tissue derived in Step S104 of the overall imaging process (see FIG. 10), the imaging conditions, and the first radiation detector 20A from the storage unit 86. In addition, the CPU 80 acquires the scattered ray correction data 95 associated with the composition of the soft tissue derived in Step S104 of the overall imaging process (see FIG. 10), the imaging conditions, and the second radiation detector 20B from the storage unit 86. Further, for example, the console 18 may acquire the scattered ray correction data 95 from an external system connected through the network.

Then, in Step S141B, the CPU 80 generates image data indicating a temporary scattered ray image for the first radiographic image, using the scattered ray correction data 95 associated with the imaging conditions and the first radiation detector 20A. Specifically, the CPU 80 derives the amount and spread of scattered rays for each pixel of the first radiographic image, using the scattered ray correction data 95, and performs a convolution operation for the derived amount and spread of scattered rays to generate image data of the first radiographic image in which the scattered ray components included in the first radiographic image have been corrected.

In addition, similarly, for the second radiographic image, the CPU 80 generates image data of the second radiographic image in which the scattered ray components included in the second radiographic image have been corrected, using the scattered ray correction data 95 associated with the imaging conditions and the second radiation detector 20B.

Then, in Step S142, the CPU 80 generates DXA image data, using the corrected first radiographic image data and second radiographic image data subjected to the correction in Step S141B.

Therefore, according to the console 18 of this embodiment, the CPU 80 functions as an example of a correction unit according to the present disclosure and the scattered ray components caused by the scattered rays of the radiation R included in each of the first radiographic image and the second radiographic image are corrected. As a result, it is possible to improve the accuracy of deriving bone density.

As described above, in the console 18 according to each of the above-described embodiments, the CPU 80 functions as an acquisition unit and a derivation unit. The acquisition unit acquires the first radiographic image and the second radiographic image respectively generated by the first radiation detector 20A and the second radiation detector 20B which are irradiated with the radiation R with the first energy emitted from the radiation source 14 in the preliminary imaging before the main imaging from the radiography apparatus 16 including the first and second radiation detectors 20A and 20B in which a plurality of pixels 32, each of which includes the sensor unit 32A that generates a larger amount of charge as it is irradiated with a larger amount of radiation R which has been emitted from the radiation source 14 and then transmitted through the subject W, are arranged and which are arranged in the direction in which the radiation R is emitted. The derivation unit derives the composition of a soft tissue of the subject W, using the first radiographic image and the second radiographic image acquired by the acquisition unit, and derives the second energy of the radiation R emitted from the radiation source 14 in the main imaging according to the derived composition of the soft tissue.

As the percentage of muscle becomes higher than the percentage of fat, the degree of energy separation by the radiation R after the radiation R is transmitted through the subject W becomes lower. In contrast, with the above-mentioned configuration, according to the console 18 of each of the above-described embodiments, as the percentage of muscle becomes higher, the energy of the radiation R in the main imaging becomes lower, which makes it possible to improve the separation of energy in the main imaging. Therefore, according to the console 18 of each of the above-described embodiments, it is possible to change the energy of the radiation R which has been transmitted through the subject W and then emitted to the radiography apparatus 16 to a desired state, regardless of the composition of a soft tissue of the subject W. As a result, according to the console 18 of each of the above-described embodiments, it is possible to obtain a radiographic image with desired quality in the main imaging. In addition, according to the console 18 this embodiment, since a high-quality radiographic image used for deriving bone density using the DXA method is obtained, it is possible to improve the accuracy of deriving bone density.

In particular, in a case in which the radiographic image of the subject W in a standing state is captured and the image of the proximal part of the femur is captured in order to derive bone density, in the subject W with a large amount of fat, fat may sag down to the root of the femur corresponding to a region used to derive bone density and overlap. In this case, according to the console 18 of each of the above-described embodiments, it is possible to change the energy of the radiation R emitted to the radiography apparatus 16 in the main imaging to a desired state, regardless of the percentage (amount) of fat. Therefore, according to the console 18 of each of the above-described embodiments, it is possible to obtain a radiographic image with desired quality in the main imaging, regardless of the subject W. In addition, it is possible to improve the accuracy of deriving bone density.

Further, the first radiographic image and the second radiographic image for deriving the composition of the soft tissue of the subject W are preferably obtained in the preliminary imaging. Therefore, the quality of the first radiographic image and the second radiographic image obtained by the preliminary imaging may be lower than the quality of the first radiographic image and the second radiographic image obtained by the main imaging. For example, the number of pixels in each of the first radiographic image and the second radiographic image obtained by the preliminary imaging may be smaller than the number of pixels in each of the first radiographic image and the second radiographic image obtained by the main imaging. In this case, for example, the size of the first radiographic image and the second radiographic image in the preliminary imaging may be set to the minimum size including the soft region (see FIG. 12) which is a region for deriving the composition of the soft tissue to reduce the number of pixels.

For example, the resolution of the first radiographic image and the second radiographic image obtained by the preliminary imaging may be lower than the resolution of the first radiographic image and the second radiographic image obtained by the main imaging. In this case, for example, the radiography apparatus 16 may read charge in units of a plurality of adjacent pixels to generate each of the first radiographic image and the second radiographic image in the individual imaging process of the preliminary imaging and may read charge in units of one pixel to generate each of the first radiographic image and the second radiographic image in the individual imaging process of the main imaging. In other words, the radiography apparatus 16 may regard a group of a plurality of predetermined pixels as one pixel and generate the first radiographic image and the second radiographic image with low resolution in the preliminary imaging. In addition, in the individual imaging process of the preliminary imaging, for example, the control units 58A and 58B may add the charge read in units of one pixel to regard a group of a plurality of pixels as one pixel.

Figure 18:
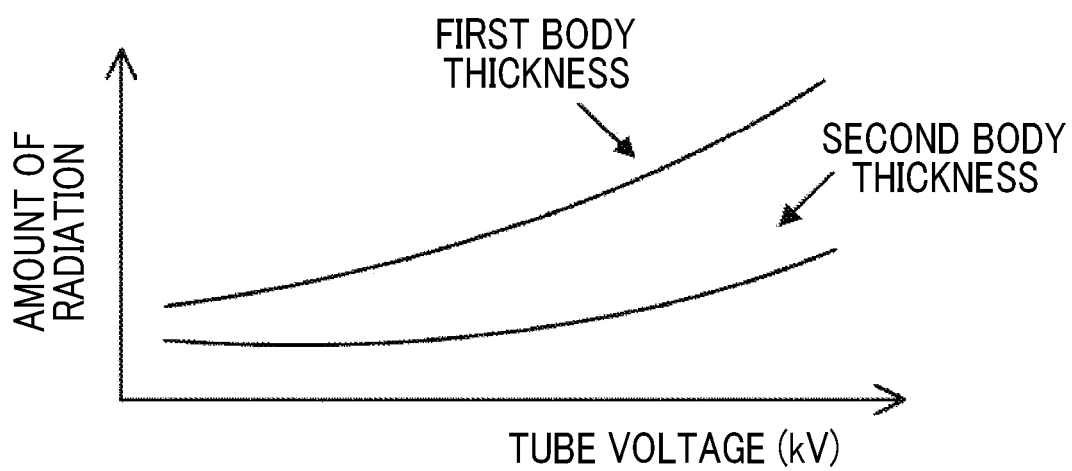
FIG. 18 is a graph illustrating a correspondence relationship between a body thickness and the amount of radiation transmitted through the subject.

In each of the above-described embodiments, the body thickness of the subject W is not considered. However, in general, the amount of radiation R transmitted and scattered ray components vary depending on the body thickness of the subject W. For example, as illustrated in FIG. 18, for the amount of radiation R after the radiation R is transmitted through the subject W, the amount of radiation R transmitted through the subject W with a first body thickness is larger than the amount of radiation R transmitted through the subject W with a second body thickness larger than the first body thickness. Therefore, it is preferable to correct the amount of radiation R emitted from the radiation source 14 and scattered ray components according to the body thickness of the subject W in addition to the composition of the soft tissue of the subject W and the imaging conditions.

For example, an example of the correspondence relationship among the body thickness, the amount of radiation, and the tube voltage illustrated in FIG. 18 may be stored in the console 18, using the first body thickness as the reference, and the CPU 80 of the console 18 may derive the amount of radiation R in the main imaging, using the stored correspondence relationship. Specifically, in FIG. 18, in a case in which the amount of radiation R emitted to the radiography apparatus 16 is desired to be equal to or more than H for the subject W with the second body thickness, the tube voltage may be equal to or greater than J (kV). In addition, in a case in which scattered ray components corresponding to the body thickness are corrected, in the second embodiment, the scattered ray correction data 95 associated with the body thickness may be stored in the storage unit 86.

Both the energy of the radiation R in the preliminary imaging and the energy of the radiation R in the main imaging may be high energy (or low energy) or may be determined according to, for example, the user's request. In a case in which the energy of the radiation R in the preliminary imaging is higher than the energy of the radiation R in the main imaging, it is possible to reduce the exposure of the subject to radiation in the preliminary imaging. In addition, in a case in which the energy of the radiation R in the preliminary imaging is lower than the energy of the radiation R in the main imaging, it is possible to improve energy separation in the preliminary imaging and to improve the accuracy of deriving the composition of the soft tissue.

In each of the above-described embodiments, after the preliminary imaging, the main imaging is performed. However, the interval between the preliminary imaging and the main imaging is not particularly limited. For example, only the main imaging may be performed, using the composition of the soft tissue derived by the preliminary imaging, after several minutes to several hours have elapsed since the end of the preliminary imaging. As such, in the console 18 according to each of the above-described embodiments, it is considered that there is no change in the composition of the soft tissue caused by the movement of the body of the subject W. Therefore, even in a case in which the movement of the body of the subject W occurs between the preliminary imaging and the main imaging, the main imaging is not affected by the movement and it is possible to optimize the energy of the radiation R in the main imaging.

In each of the above-described embodiments, the bone density of the subject W is derived using the radiographic images generated by each of two radiation detectors 20 provided in the radiography apparatus 16. Therefore, the bone density of the subject W can be derived by one operation of emitting the radiation R. As a result, it is possible to derive the bone density of the subject W while reducing the amount of radiation R emitted to the subject W.

In each of the above-described embodiments, the bone density derivation process performed by the console 18 may be performed by the control unit 58A or the control unit 58B of the radiography apparatus 16. In addition, in a case in which the radiography apparatus 16 includes an overall control unit that controls the overall operation of the control unit 58A and the control unit 58B, the overall control unit may perform the bone density derivation process. Furthermore, for example, an information processing apparatus that is connected to the console 18 through the network may perform the bone density derivation process.

In each of the above-described embodiments, the case in which an indirect-conversion-type radiation detector that converts radiation into light and converts the converted light into charge is applied to both the first radiation detector 20A and the second radiation detector 20B has been described. However, the invention is not limited thereto. For example, a direct-conversion-type radiation detector that directly converts radiation into charge may be applied to at least one of the first radiation detector 20A or the second radiation detector 20B. In addition, for example, a conversion layer that absorbs radiation and converts the radiation into charge in the direct-conversion-type radiation detector is made of amorphous selenium (a-Se) and crystalline cadmium telluride (CdTe).

In each of the above-described embodiments, the case in which the ISS radiation detectors in which the radiation R is incident from the TFT substrates 30A and 30B are applied to the first radiation detector 20A and the second radiation detector 20B, respectively, has been described. However, the invention is not limited thereto. For example, a penetration side sampling (PSS) radiation detector in which the radiation R is incident from the scintillator 22A or 22B may be applied to at least one of the first radiation detector 20A or the second radiation detector 20B.

In each of the above-described embodiments, the case in which bone density is derived using the first radiographic image data and the second radiographic image data obtained by the main imaging has been described. However, the invention is not limited thereto. For example, bone mineral content or both bone density and bone mineral content may be derived using the first radiographic image data and the second radiographic image data. In addition to the bone density and the bone mineral content, for example, other numerical values required for diagnosis may be derived using the first radiographic image data and the second radiographic image data.

In each of the above-described embodiments, the following various processors may be used as the hardware structure of processing units for performing various processes, such as an acquisition unit, a derivation unit, and a correction unit. The various processors include, for example, a programmable logic device (PLD), such as a field-programmable gate array (FPGA), which is a processor whose circuit configuration can be changed after manufacture and a dedicated electric circuit, such as an application specific integrated circuit (ASIC), which is a processor having a dedicated circuit configuration designed to perform a specific process, in addition to the CPU which is a general-purpose processor that executes software (program) to function as various processing units as described above.

One processing unit may be formed by one of the various processors or may be formed by a combination of two or more processors of the same type or different types (for example, a combination of a plurality of FPGAs and a combination of a CPU and an FPGA). In addition, a plurality of processing units may be formed by one processor. A first example of the configuration in which the plurality of processing units are formed by one processor is an aspect in which one or more CPUs and software are combined to form one processor and the processor functions as a plurality of processing units. A representative example of the aspect is a computer such as a client apparatus or a server. A second example of the configuration is an aspect in which a processor that implements all of the functions of a system including the plurality of processing units with one integrated circuit (IC) chip is used. A representative example of the aspect is a system-on-chip (SoC). As such, the hardware structure of various processing units is formed by using one or more of the various processors.

Specifically, an electric circuit (circuitry) obtained b combining circuit elements, such as semiconductor elements, may be used as the hardware structure of these various processors.

In each of the above-described embodiments, the aspect in which the overall imaging processing program is stored (installed) in the storage unit 86 in advance has been described. However, the invention is not limited thereto. The overall imaging processing program may be recorded on a recording medium, such as a compact disk read only memory (CD-ROM), a digital versatile disk read only memory (DVD-ROM), or a universal serial bus (USB) memory, and then provided. In addition, the overall imaging processing program may be downloaded from an external apparatus through the network.

In each of the above-described embodiments, the aspect in which the individual imaging processing program is stored in the ROM of the memory 62 in the control unit 58A (control unit 58B) in advance has been described. However, the invention is not limited thereto. The individual imaging processing program may be recorded on the recording medium and then provided. In addition, the individual imaging processing program may be downloaded from an external apparatus through the network.

In addition, for example, the configuration and operation of the radiography apparatus 16 and the console 18 described in the above-described embodiments are illustrative and may be changed according to the situation without departing from the scope and spirit of the invention. For example, in a case in which the user changes at least one of the first radiographic image or the second radiographic image obtained by the main imaging to desired quality, the technique according to the present disclosure may be applied.

What is claimed is:

1. An image processing apparatus comprising:
a processor configured to:
   acquire a first radiographic image and a second radiographic image respectively generated by a first radiation detector and a second radiation detector which are irradiated with radiation with first energy emitted from a radiation source in preliminary imaging before main imaging from a radiography apparatus including the first and second radiation detectors in which a plurality of pixels, each of which includes a conversion element that generates a larger amount of charge as it is irradiated with a larger amount of radiation which has been emitted from the radiation source and then transmitted through a subject, are arranged and which are arranged in a direction in which the radiation is emitted; and
   derive a composition of a soft tissue of the subject, using the first and second radiographic images that are acquired, and derive second energy of the radiation emitted from the radiation source in the main imaging according to the derived composition of the soft tissue.

2. The image processing apparatus according to claim 1, wherein, as a percentage of muscle becomes higher than a percentage of fat in the composition of the soft tissue, the second energy becomes lower.

3. The image processing apparatus according to claim 1, wherein the processor is further configured to derive the composition of the soft tissue on the basis of a pixel value of a region corresponding to the soft tissue of the subject in the first radiographic image and a pixel value of a region corresponding to the soft tissue of the subject in the second radiographic image.

4. The image processing apparatus according to claim 1, wherein the processor is further configured to acquire a third radiographic image and a fourth radiographic image which are respectively generated by the first and second radiation detectors of the radiography apparatus irradiated with the radiation with the second energy emitted from the radiation source in the main imaging.

5. The image processing apparatus according to claim 4, wherein a number of pixels in each of the first radiographic image and the second radiographic image is less than a number of pixels in each of the third radiographic image and the fourth radiographic image.

6. The image processing apparatus according to claim 5, wherein a size of each of the first radiographic image and the second radiographic image corresponds to a size of a region that is predetermined in order to derive the composition of the soft tissue.

7. The image processing apparatus according to claim 4, wherein each of the first radiographic image and the second radiographic image has a lower resolution than each of the third radiographic image and the fourth radiographic image.

8. The image processing apparatus according to claim 7, wherein each of the first radiographic image and the second radiographic image is a radiographic image generated by reading charge in units of a plurality of predetermined pixels, and
each of the third radiographic image and the fourth radiographic image is a radiographic image generated by reading charge in units of one pixel.

9. The image processing apparatus according to claim 4, wherein the processor is further configured to correct scattered ray components caused by scattered rays of the radiation included in each of the third radiographic image and the fourth radiographic image, using scattered ray correction data corresponding to the composition of the soft tissue.

10. The image processing apparatus according to claim 4, wherein the processor is further configured to derive at least one of bone density or bone mineral content, using the third radiographic image and the fourth radiographic image that is acquired.

11. The image processing apparatus according to claim 1, wherein the first energy is higher than the second energy.

12. The image processing apparatus according to claim 1, wherein the first energy is lower than the second energy.

13. The image processing apparatus according to claim 1, wherein the preliminary imaging and the main imaging are performed for the subject in a standing state.

14. The image processing apparatus according to claim 1, wherein each of the first and second radiation detectors comprises a light emitting layer that is irradiated with the radiation and emits light,
the plurality of pixels of each of the first and second radiation detectors receive the light, generate charge, and accumulate the charge, and
the light emitting layer of one of the first and second radiation detectors which is provided on an incident side of the radiation includes CsI and the light emitting layer of the other radiation detector includes GOS.

15. A radiography system comprising:
an image processing apparatus that comprises:
   a processor configured to:
      acquire a first radiographic image and a second radiographic image respectively generated by a first radiation detector and a second radiation detector which are irradiated with radiation with first energy emitted from a radiation source in preliminary imaging before main imaging from a radiography apparatus including the first and second radiation detectors in which a plurality of pixels, each of which includes a conversion element that generates a larger amount of charge as it is irradiated with a larger amount of radiation which has been emitted from the radiation source and then transmitted through a subject, are arranged and which are arranged in a direction in which the radiation is emitted, and
      derive a composition of a soft tissue of the subject, using the first and second radiographic images that is acquired, and derive second energy of the radiation emitted from the radiation source in the main imaging according to the derived composition of the soft tissue; and a radiography apparatus that outputs a first radiographic image and a second radiographic image to the image processing apparatus.

16. An image processing method comprising:

acquiring a first radiographic image and a second radiographic image respectively generated by a first radiation detector and a second radiation detector which are irradiated with radiation with first energy emitted from a radiation source in preliminary imaging before main imaging from a radiography apparatus including the first and second radiation detectors in which a plurality of pixels, each of which includes a conversion element that generates a larger amount of charge as it is irradiated with a larger amount of radiation which has been emitted from the radiation source and then transmitted through a subject, are arranged and which are arranged in a direction in which the radiation is emitted;

deriving a composition of a soft tissue of the subject, using the acquired first and second radiographic images; and deriving second energy of the radiation emitted from the radiation source in the main imaging according to the derived composition of the soft tissue.

\* \* \* \* \*